(12) United States Patent
Fan et al.

(10) Patent No.: US 7,693,369 B2
(45) Date of Patent: Apr. 6, 2010

(54) HOLLOW CORE OPTICAL RING RESONATOR SENSOR, SENSING METHODS, AND METHODS OF FABRICATION

(75) Inventors: Xudong Fan, Columbia, MO (US); Ian M. White, Columbia, MO (US); Hesam Oveys, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 11/733,119

(22) Filed: Apr. 9, 2007

(65) Prior Publication Data

US 2007/0237460 A1 Oct. 11, 2007

Related U.S. Application Data

(60) Provisional application No. 60/790,467, filed on Apr. 7, 2006.

(51) Int. Cl.
*G02B 6/26* (2006.01)
(52) U.S. Cl. .............................. 385/32; 385/2
(58) Field of Classification Search .................. 372/94; 385/27, 30; 356/461
See application file for complete search history.

(56) References Cited

U.S. PATENT DOCUMENTS

| 4,820,008 | A  | * | 4/1989  | Malvern ...................... 385/27  |
| 4,996,884 | A  | * | 3/1991  | Lessing ....................... 73/800  |
| 5,663,790 | A  | * | 9/1997  | Ekstrom et al. ............. 356/128    |
| 6,480,282 | B1 | * | 11/2002 | Chinowsky et al. ......... 356/445      |
| 6,515,749 | B2 | * | 2/2003  | Pipino ......................... 356/440 |
| 6,657,731 | B2 | * | 12/2003 | Tapalian et al. ............. 356/480   |
| 6,888,987 | B2 | * | 5/2005  | Sercel et al. .................. 385/39  |
| 6,891,996 | B2 | * | 5/2005  | Sercel et al. .................. 385/30  |
| 6,891,997 | B2 | * | 5/2005  | Sercel et al. .................. 385/30  |
| 6,901,101 | B2 | * | 5/2005  | Frick ........................... 372/92  |
| 7,043,115 | B2 | * | 5/2006  | Frick ........................... 385/27  |
| 7,046,362 | B2 | * | 5/2006  | Lehmann et al. ............ 356/437     |
| 7,106,917 | B2 | * | 9/2006  | Painter et al. .................. 385/2  |
| 2002/0018212 | A1 | * | 2/2002  | Bennett et al. .............. 356/483  |
| 2002/0037132 | A1 | * | 3/2002  | Sercel et al. .................. 385/30 |
| 2002/0041730 | A1 | * | 4/2002  | Sercel et al. .................. 385/30 |

(Continued)

FOREIGN PATENT DOCUMENTS

JP         63040810 A   *   2/1988

(Continued)

OTHER PUBLICATIONS

Zhu et al., Design of solid-core microstructured optical fiber with steering-wheel air cladding for optimal evanescent-field sensing, 2006, Optics Express, vol. 14, No. 8, p. 3541.*

*Primary Examiner*—Frank G Font
*Assistant Examiner*—Peter Radkowski
(74) *Attorney, Agent, or Firm*—Polsinelli Shughart PC

(57) ABSTRACT

The present invention is directed to hollow core optical ring resonators (HCORRs), methods of fabricating HCORRs, and methods of using HCORRs in sensing applications. In particular, the evanescent field and whispering gallery modes of the HCORRs may be used to detect a target analyte within the hollow core of the HCORR. Other features of the present invention include utilizing the HCORR as part of a multiplex sensing device, including using the HCORR in capillary electrophoresis and chromatography applications.

24 Claims, 24 Drawing Sheets

U.S. PATENT DOCUMENTS

2002/0068018 A1* 6/2002 Pepper et al. ............ 422/82.05
2002/0081055 A1* 6/2002 Painter et al. ................. 385/2
2002/0172457 A1* 11/2002 Tapalian et al. .............. 385/30
2003/0107739 A1* 6/2003 Lehmann et al. ............ 356/437
2003/0109055 A1* 6/2003 Lehmann et al. ............ 436/164
2006/0072875 A1* 4/2006 Bhagavatula et al. .......... 385/30
2007/0269901 A1* 11/2007 Armani et al. .............. 436/172

FOREIGN PATENT DOCUMENTS

WO    WO 2006083691 A1 * 8/2006

* cited by examiner

Microdisk-shaped ring resonator on a wafer substrate

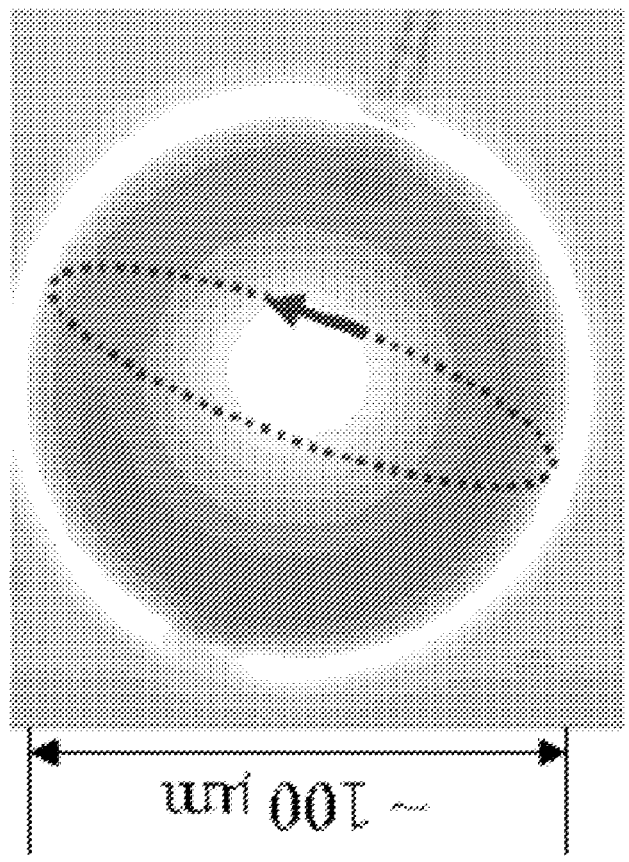
FIG. 3B  Stand-alone microsphere ring resonator

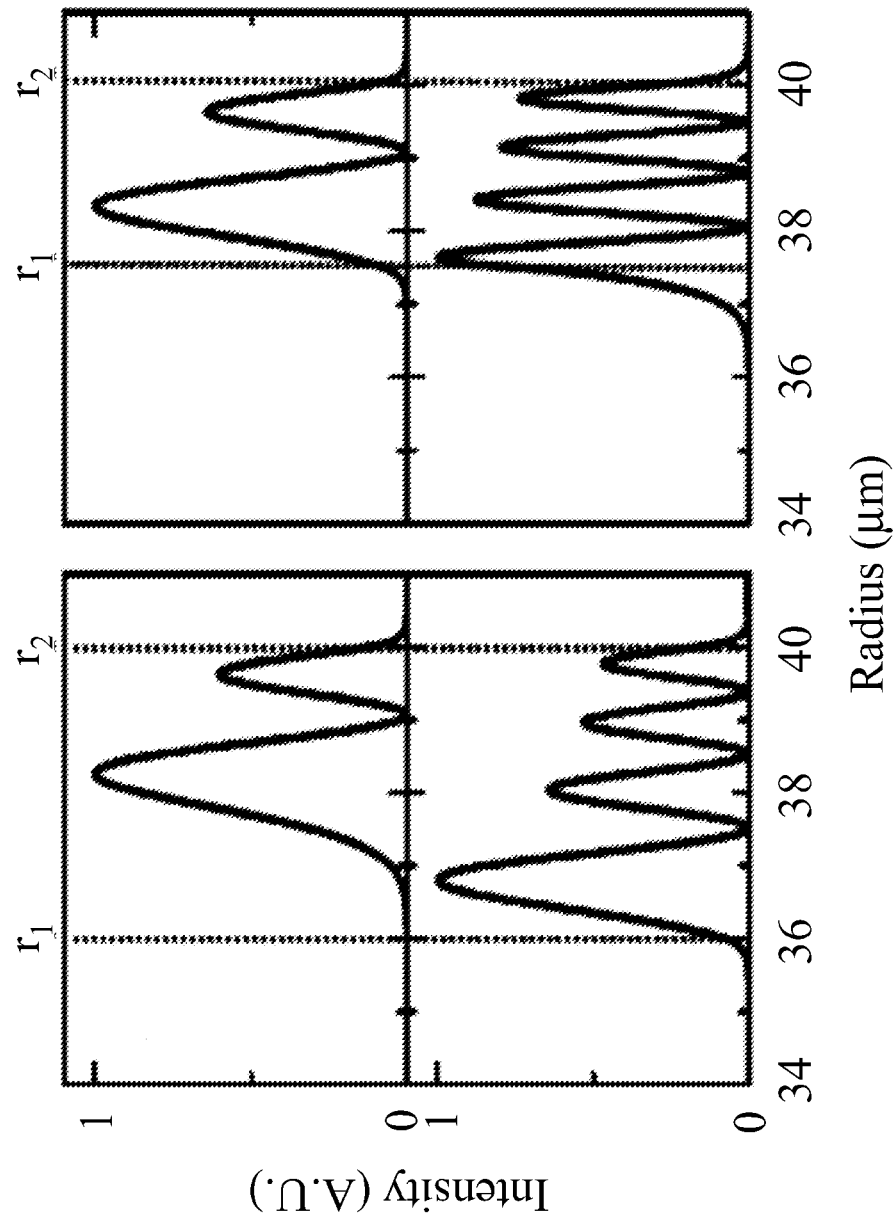

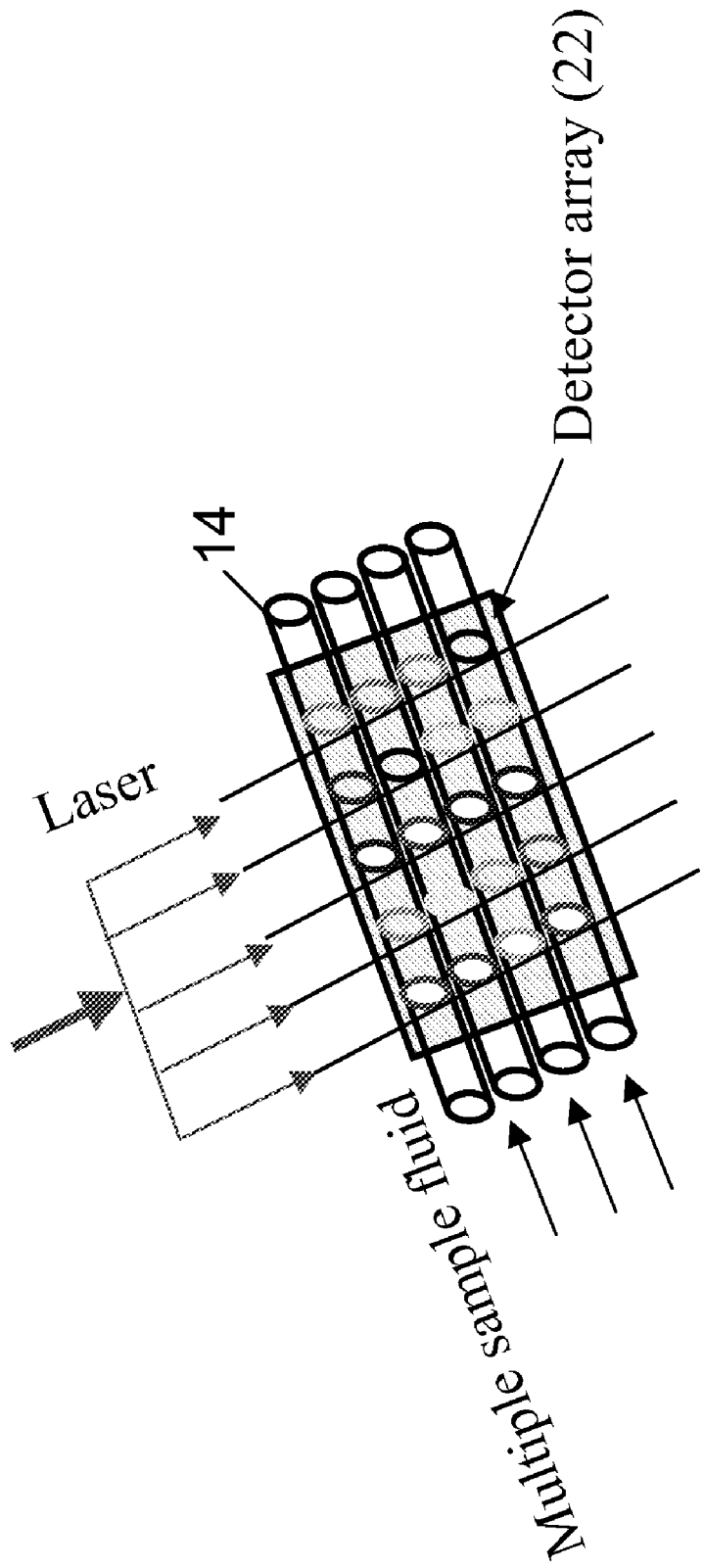

Laser to drill hole and "write" features

Top view

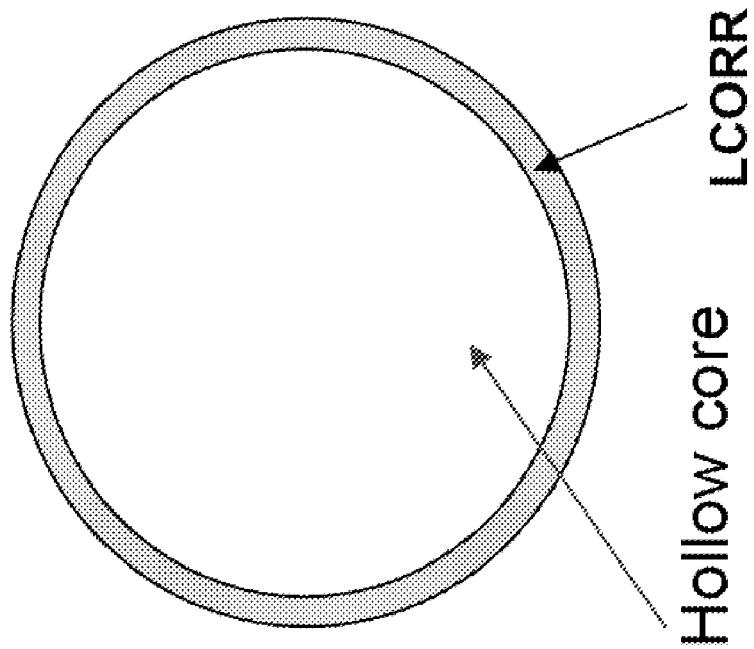
FIG. 13 — Hollow core, LCORR
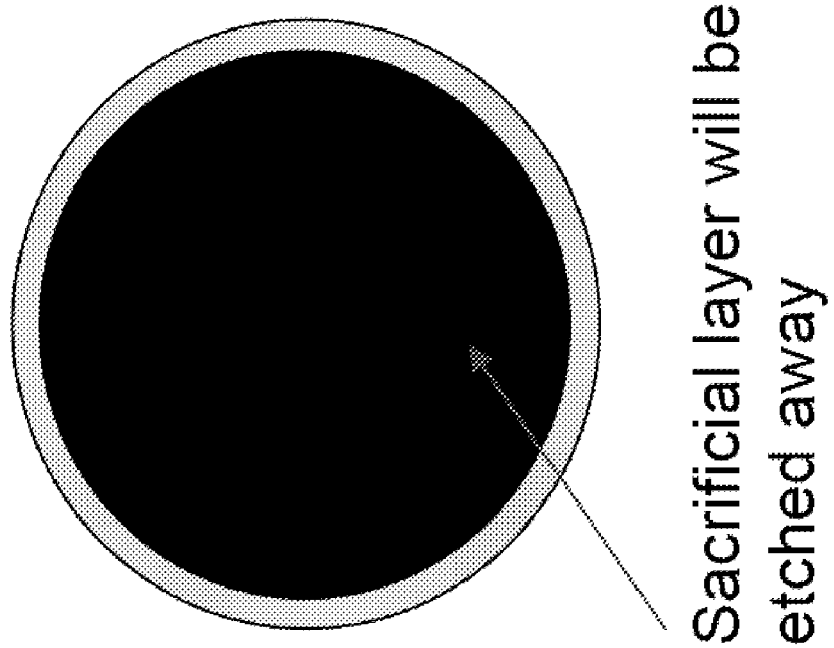
FIG. 12 — Sacrificial layer will be etched away

HOLLOW CORE OPTICAL RING RESONATOR SENSOR, SENSING METHODS, AND METHODS OF FABRICATION

CROSS REFERENCE TO RELATED APPLICATIONS

This application claims priority from U.S. Provisional Application Ser. No. 60/790,467 filed on Apr. 7, 2006, which is hereby incorporated by reference in its entirety. Additionally, all patents, published patent applications, and other references cited throughout this specification are hereby incorporated by reference in their entireties.

FIELD OF THE INVENTION

The present invention is directed generally to hollow core optical ring resonators (HCORRs), systems incorporating HCORRs, as well as methods of fabricating HCORRs. The present invention is also directed to methods of using HCORRs as whispering-gallery mode evanescent-wave sensors for small and large molecule detection, and for other sensing applications.

BACKGROUND OF THE INVENTION

In the past, evanescent wave sensors have generally been limited to fiber/waveguides, microspheres, and microdisks. The older fiber/waveguide sensors required large sample volumes. The relatively newer stand-alone microspheres and microdisks (or microrings) fabricated on a substrate were smaller and had greater sensitivity than the fiber/waveguides, but microspheres are difficult to mass-produce and microdisks (or microrings) suffered from degraded Q-factors due to surface roughness created during the fabrication process. Importantly, all of the evanescent wave sensors suffered from problems associated with efficiently combining fluidics and photonics, such that the two aspects did not interfere with one another (e.g. issues relating to effective fluid delivery, optical signal reliability, and high-throughput capability). These problems were related to the fact that the evanescent field sensors of the past attempted to detect compositions located on the exterior of the sensor. None of the evanescent wave sensors in the prior art contemplated using an optical ring resonator with a hollow core, which has the capability of detecting compositions on the interior surface of the sensor.

The first generation of optical evanescent-wave sensors, fiber/waveguide sensors, has been in existence for over twenty years and has found applications in many fields [1]. These devices have been characterized as being immune to electromagnetic waves and capable of performing remote sensing. A generic configuration of a first generation fiber/waveguide sensor is depicted in FIG. 1. In the illustration, the outside surface of the fiber/waveguide was first immobilized with a layer of biorecognition molecules such as antibodies. The guided light traveling along the inside of the fiber/waveguide had an evanescent field extending outwardly from the sensor into the surrounding medium (e.g., water) for approximately 100 nm and was capable of interacting with the bio/chemical molecules near the fiber/waveguide external surface. The guided light changed in response to tiny modifications in refractive index near the fiber/waveguide surface when target analytes were captured; the modifications in the optical signal could be detected at the output as a sensor signal. The sensitivity was determined by light-analyte interaction since the sensing signal was accumulative in nature. A longer interaction length resulted in higher sensitivity, and hence a lower detection limit. In these fiber/waveguide sensors, the light passed the fiber/waveguide only once. Consequently, fiber/waveguide sensors were required to be a few centimeters in length so they could achieve the adequate sensitivity [2,3]. The length and bulky characteristics of fiber/waveguide sensors also created significant problems by increasing the required sample volume and reducing the sensor multiplexing capabilities.

One solution to the short interaction problem of fiber/waveguide sensors was to have the light at the output coupled back to the input in order to recycle the light. This idea evolved into "ring resonator sensors," in which the light circulates at the inner surface of the ring-shaped waveguide repetitively. This circulation mode of the light was called the "whispering gallery mode" (WGM) [4]. In a ring resonator, whispering gallery modes (WGMs) form due to total internal reflection of the light along the curved boundary surface. In a ring resonator, the evanescent field of the WGM extends into the surrounding medium for approximately 100 nm and is capable of interacting with the molecules on the ring resonator surface in the same manner as in fiber/waveguide sensors.

Optical ring resonator sensors have been characterized by their remote sensing capabilities, improved sensing performance, and immunity to electromagnetic waves. As compared to a simple fiber/waveguide design, the resonating nature of the circulating light has significantly enhanced the light-analyte interaction, and hence the sensitivity. Furthermore, the effective light-analyte interaction length of a ring resonator has not been limited by the sensor physical size, but rather by the number of circulations of the light supported by the ring resonators, which is characterized by the resonator quality factor, or Q-factor parameter.

Generally, there have been two types of ring resonators used in sensor development—based on either microsphere shaped or microdisk/microring shaped structures (FIG. 3). Since microdisk and microring structures are very similar, for simplicity only the microdisk resonator is used as an example. The Q-factor ranges from $10^3$ to $10^4$ for microdisk based ring resonators and exceeds $10^6$ for microsphere based ring resonators [4-13]. Although the size of those ring resonators is only a few tens to a few hundreds of microns in diameter, the effective interaction length can be 10 cm to 1,000 cm due to the high Q-factor. Thus, a ring resonator can deliver sensing performance equivalent to a waveguide while using orders of magnitude less surface area, which results in a significantly reduced sample volume. Furthermore, due to small size of the ring resonators, high-density sensor integration becomes possible.

Recently, the detection of bio/chemical molecules such as protein, DNA, enzyme, and mercuric ions with microsphere ring resonator sensors has been demonstrated by several research groups [6-13]. The detection limit of biomolecules and the refractive index change of solutions respectively are shown to be on the order of 1 $pg/mm^2$ and $10^7$ refractive index units (RIU), much better than that of fiber/waveguide sensors [2,3,9,11-13].

Ring resonator sensor development encompasses two essential parts, photonics and fluidics, which deal with delivering the light and the aqueous samples to the sensing head, respectively. It is important that the fluidics portion is incorporated without sacrificing the photonic sensing performance such as multiplexing capability and high Q-factor. While disk-shaped ring resonators can be mass-produced with photolithographic technologies in an array format, they suffer from a degraded Q-factor due to surface roughness created during the fabrication process. Moreover, an effective fluidics system that is separately fabricated from the photonics has yet to be demonstrated with microdisks.

On the other hand, microsphere resonators have much higher Q-factors. Nevertheless, integration of microsphere arrays and the subsequent incorporation of fluidics, however, have proven to be very challenging because of the spheres' 3-D configuration and fabrication process. As a result, it appears that neither of these ring resonator technologies is optimal for practical sensing systems.

Therefore, there is a need for novel sensor architecture to incorporate the fluidics without sacrificing the photonic sensing performance. There is also a need for a better method of production, which does not suffer from surface roughness and degraded Q-factor. There is also a need for novel sensor architecture for easy and practical fabrication. There is yet another need for novel sensor architecture capable of densely multiplexing into a small array to allow for simultaneous detection of multiple target analytes, as well as redundant testing. The present invention has unique structural components as well as functional attributes that solve the problems associated with combining photonics and fluidics. Moreover, the present invention does not suffer from degraded Q-factor, which has been a recognized problem in developing ring resonators, typically due to surface roughness induced during the fabrication processes. Accordingly, there is a significant need for the hollow core optical ring resonator of the present invention, which provides a structure that is capable of incorporating fluidics without sacrificing photonic sensing performance.

SUMMARY OF THE INVENTION

The present invention provides a hollow core optical ring resonator (HCORR), which possesses the meritorious high sensitivity and low sample consumption of ring resonators, and at the same time, is highly compatible with well-developed capillary technologies for fluid delivery. As a result of its compatibility with liquid fluidics, the HCORR is alternatively referred to as an LCORR (i.e. liquid core optical ring resonator), although the HCORR is not limited to testing liquid samples. The inventive HCORR comprises a hollow optical tubing material with an outer diameter ranging from about 10 µm to about 1000 µm (preferably from about 30 µm to about 500 µm, more preferably from about 50 µm to about 300 µm) and a wall thickness ranging from about 1 µm to about 20 µm (preferably from about 1 µm to about 10 µm, more preferably from about 2 µm to about 5 µm). The circular cross section of the hollow optical tubing material forms a ring resonator that supports the whispering gallery modes (WGMs), which has the evanescent field extending into the hollow core, allowing for repetitive interaction with the target analyte or sample carried inside the capillary. The HCORR may be made of an optically transparent material, such as glass, transparent polymer, transparent semiconductors, or other dielectric materials. The HCORR may also be characterized as having smooth inner and outer wals, which increase the sensitivity of the HCORR.

The present invention also provides methods for manufacturing the HCORR to achieve the desired optical properties. The preferred methods for fabrication of HCORR are mechanical pulling, chemical etching, or combination of both of an optical tube with hollow core to reduce its wall to a predetermined thickness. One preferred embodiment comprises the steps: (1) pre-etching the outer surface of the provided optical tube by submerging said tube into a pre-etching solution to produce a pre-etched tube with a reduced outer diameter, (2) pulling the pre-etched tube at one or both ends, while heating the pre-etched tube to produce an elongated tube, (3) post-etching the elongated tube by running a post-etching solution into the hollow core of the elongated tube to produce the HCORR with desired wall thickness. Post-etching can also be completed by etching the elongated tube from inside or outside surfaces to produce the HCORR with the desired wall thickness.

Additionally, the present invention provides a HCORR sensor system and method of using such system. The inventive HCORR sensor system comprises (a) a light source, said light source being capable of emitting laser light at a single or plurality wavelength(s), (b) an HCORR with a wall at a certain predetermined thickness, said light source being positioned to emit light into the HCORR via free-space coupling or via a fiber/waveguide and said HCORR emitting at least a portion of said laser light therefrom, and (c) a detector detecting the light emitted from said HCORR and/or said fiber/waveguide.

BRIEF DESCRIPTION OF THE DRAWINGS

FIG. 3(A) depicts microdisk based ring resonator; FIG. 3(B) depicts microsphere based ring resonator.

FIG. 4(A) depicts a sample detection scheme using HCORR.

FIGS. 5($a$) & (b) shows exemplary light intensity distributions at different radial modes for two HCORRs with different wall thickness.

FIG. 12 shows a possible fabrication method for HCORR, selective etching.

FIG. 13 shows a cross-sectional view of an HCORR, produced by the fabrication method of mechanical pulling.

DETAILED DESCRIPTION OF THE INVENTION

Figure 1:
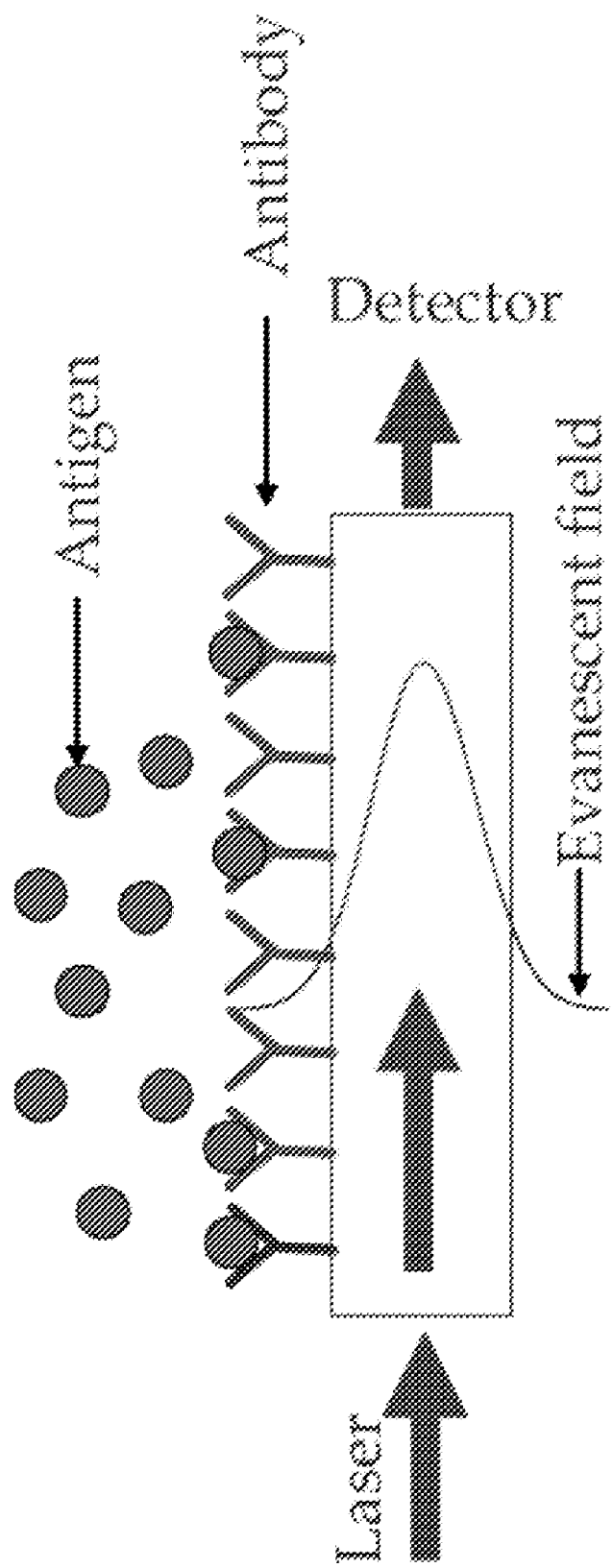
FIG. 1 illustrates the general mechanism of the fiber/waveguide sensor.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

1. Hollow Core Optical Ring Resonators (HCORRs)

The present invention provides a hollow core optical ring resonator (HCORR) having an optical tube with an outer surface and an inner surface, with the inner surface forming a hollow core. The HCORR has an outer diameter ranging from about 10 µm to about 1000 µm and a wall thickness ranging from about 1 µm to about 20 µm. In particular, the HCORR may also have an outer diameter ranging from about 30 µm to 500 µm or from about 50 µm to 300 µm. The wall thickness may also range from about 1 µm to about 10 µm, and also from about 2 µm to about 5 µm. The outer and inner surfaces of the optical tube are preferably smooth, which has the effect of reducing light scattering (i.e. noise) and improving the sensitivity of the HCORR.

The HCORR may be contacted with a light source (e.g. a tunable laser diode running through a fiber taper), which in turn produces an optical signal with an evanescent field and whispering gallery modes (WGMs) within the HCORR. The WGMs in the HCORR may be excited through a variety of different configurations, including when the light source is delivered to the HCORR via free space. The optical signal of the HCORR is capable of interacting with both the solid portion of the optical tube, as well as the hollow core or void area formed by the inner surface. In particular, the optical signal is also capable of interacting with analyte substrates and/or target analytes that may be located inside the fluidic channel formed by the hollow core. In particular, compositions with liquids or gases may be passed through the fluidic channel. Alternatively, analyte substrates or target analytes may be pumped through the fluidic channel or affixed (mechanically or chemically) to the inner surface that forms the hollow core. (See, e.g., FIG. 4B and FIG. 16). As such, there is an optical signal (the optical input signal) which is connected to the HCORR, and then another optical signal (the optical output signal) that leaves the HCORR. The presence of target analytes within the hollow core may be determined by comparing the optical input with the optical output, and evaluating any differences in refractive index or mode—for example, by analyzing the optical signals using the Mie theory.

The HCORR is not restricted to having a circular or elliptical tube shape. In particular, the HCORR may be polygonal or elliptical shaped. Similarly, the HCORR may be formed from a variety of compositions including: dialectric materials, glass, quartz, fused silica, borosilicate, optical plastics, polymer materials that are transparent in the UV, visible, or near infrared up to far infrared, PDMS, semiconductor materials that are transparent in the visible or near infrared, GaAs, InGaAs, photonic crystal structures, or any mixtures thereof.

The HCORR may be utilized in a sensor assay configuration. In this context, an HCORR is contacted by a fiber taper associated with a light source such as a tunable diode laser. The fiber taper may be arranged transverse to the HCORR or in any manner that produce whispering gallery modes within the HCORR. The HCORR may also be in contact with a photodetector and a data acquisition (DAQ) card in a computer, such that the optical signal produced by the guided light source is passed through the HCORR and is collected as an output signal for the HCORR (e.g. a baseline signal, control signal, test signal). This procedure of guiding light into the HCORR, having the light reflect off the surfaces of the HCORR ring resonator, and then collecting and quantitating the optical signal by a photodetector-DAQ-computer device, may be repeated in order to detect whether there is a target analyte or analyte substrate within the hollow core. Specifically, the optical signal of the HCORR may be modulated (e.g. changes in refractive index or mode) by the presence of a target analyte within the hollow core such that the resulting optical signal collected by the photometer may be used to identify the presence and/or quantity of a target analyte. Alternatively, there may be two separate light sources passing through an HCORR (e.g. at different points along a capillary), one of which is used as a control signal and the other is used as a test signal to determine whether a target analyte is present. An equivalent method would be to use two separate HCORRs, pass a guided light source through both HCORRs, collect the resulting optical signals as described above, and use one HCORR as the control and the other to detect the presence of target analytes.

Accordingly, the present invention provides a sensing architecture centered upon hollow core optical ring resonators (HCORRs). In particular, one unique element of the HCORR is the hollow core that allows for the separate engineering of fluidics and photonics, which eliminates many of the problems associated with integrating both systems simultaneously at the same surface. Evanescent wave sensors in the prior art have not utilized such a hollow core feature. Moreover, these same wave sensors have also been unable to provide the necessary reduced wall thicknesses (e.g. from about 1 µm to about 20 µm) to carry out the presently claimed invention. The older evanescent wave sensors required light delivery and fluid delivery at the same surface, which entangled the separate and contradicting requirements of the light and fluid delivery.

The HCORR's sensitivity may be increased by reducing the thickness of the optical tube. The methods of fabricating the HCORR also allow the interior surface of the hollow core to be smooth, which also improves the Q-factor and sensitivity of the device. Because the hollow core is adjacent to the thin wall of the optical tube, the hollow core and any contents therein (e.g. target analytes, analyte substrates, test samples) are capable of interacting with the evanescent field and whispering gallery modes associated with the HCORR when coupled with a guided light source. As mentioned above, the HCORR may be used either in the presence or in the absence of liquid samples. Test samples that may be passed through the HCORR's hollow core include liquids, gases, solids, and combinations thereof (e.g. colloidal mixtures including bodily fluids such as blood and urine).

Figures 4A, 4B:
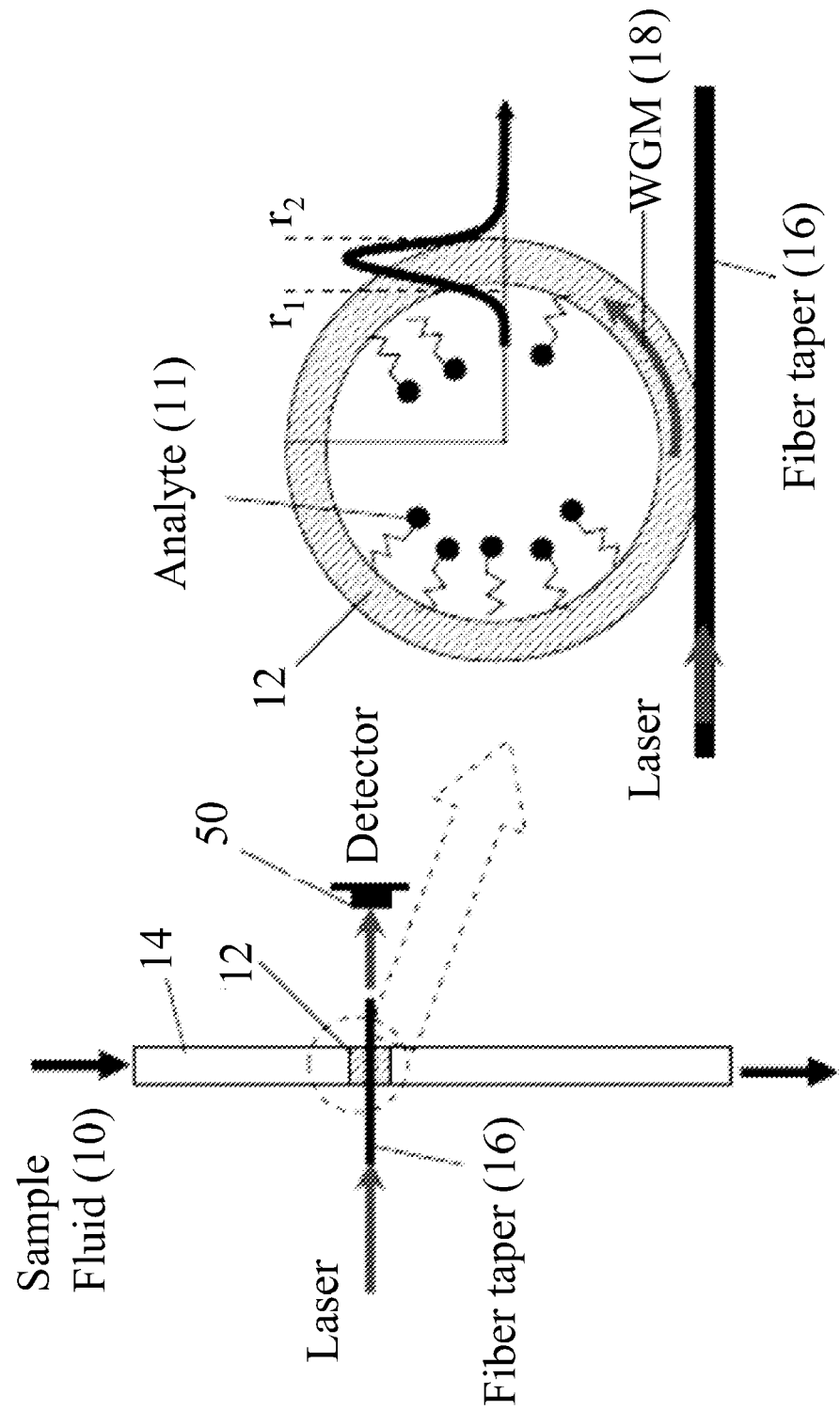
FIGS. 4(A) & (B) illustrate the concept of HCORR.
FIG. 4(B) illustrates a magnified view of a cross section of an individual HCORR.

The concept of the HCORR is illustrated in FIGS. 4(A) and (B). FIG. 4(A) depicts a detection scheme using HCORRs. During sample detection, the sample fluid (10) is delivered through the hollow-core of a capillary, each section of which represents an individual HCORR (12) and collectively HCORRs (14), whereas the whispering gallery mode (WGM) of each constituent HCORR (12) is launched through horizontally arranged optical fiber tapers or waveguides (16). The HCORR relies on the presence of the evanescent field of the WGM in the core to detect the refractive index change near the interior surface.

FIG. 4(B) illustrates a magnified view of a cross section of one HCORR (12) and shows that the evanescent field of the WGM (18) interacts with the analytes (11) in the sample fluid (10) near the interior surface of the HCORR (12). The radial distribution of the WGM of an HCORR can be described by Mie theory [14]:

$$E_{m,l}(r) = \begin{cases} AJ_m(k_0^{(l)}n_1 r) & (r \leq r_1) \\ BJ_m(k_0^{(l)}n_2 r) + CH_m^{(1)}(k_0^{(l)}n_2 r) & (r_1 \leq r \leq r_2) \\ DH_m^{(1)}(k_0^{(l)}n_3 r) & (r \geq r_2) \end{cases} \quad (1)$$

where Jm and Hm(1) are the mth Bessel function and the mth Hankel function of the first kind, respectively. The refractive indices of the core, wall, and the surrounding medium are described by n1, n2, and n3. The terms r1 and r2 represent the inner and outer radius of the HCORR, respectively, and $k_0(1)$ is the amplitude of the wave vector in vacuum for the 1th order radial WGM. The equation given in Eq. (1) describes a three-layer model, in which there is the core, the wall, and the surrounding medium. This model can also be extended to include multiple layers.

FIGS. 5(a) and (b) further provide exemplary light intensity distributions at different radial modes (l) for two HCORRs with different wall thickness. The wall thickness of the HCORR in FIG. 5(a) is determined to be about 4 μm (r1=36 μm and r2=40 μm), whereas the wall thickness in FIG. 5(b) is slightly thinner, about 2.5 μm (r1=37.5 μm and r2=40 μm). The intensity distributions of the second radial TM WGMs (m=350, l=2) are depicted on the top graphs, whereas the intensity distributions of the fourth radial mode (m=350, l=4) are depicted in the bottom graphs (m is the WGM angular momentum term). Dashed lines show the interior and exterior surfaces of each HCORR. Refractive indices are n1=1.33, n2=1.45 and n3=1.0. FIGS. 5(a) and (b) illustrate that higher radial modes penetrate deeper into the core, which causes these modes to be more sensitive to the refractive index change, and the fraction of the light in the core depends strongly on the wall thickness.

Sensitivity increases with the increased HCORR diameter, in sharp contrast to the conventional ring resonators such as microspheres where the bulk refractive index sensitivity is inversely proportional to the ring size. For a given geometry of the HCORR, sensitivity is also determined by the operating wavelength. This is related to the deeper penetration depth of the evanescent field when the wavelength becomes longer. The WGM polarization also has an effect on sensitivity. For example, the 2nd order WGM with a wall thickness of 3.5 μm has a sensitivity of 19 nm/RIU at 1550 nm when the polarization is along the HCORR axis in comparison with 23.5 nm/RIU sensitivity for the same HCORR when the polarization perpendicular to the HCORR axis. Sensitivity is further dependent upon the radial mode order. The higher order radial mode has a higher evanescent field in the core of the HCORR, resulting in higher light-matter interaction.

The HCORR structure achieves dual use of the capillary as a sensor head and as a fluidic channel. As a result, the HCORR may take advantage of the high sensitivity and low sample consumption of ring resonators, and is highly compatible with well-developed capillary technologies for automated fluid delivery and sample separation.

Figure 6A:
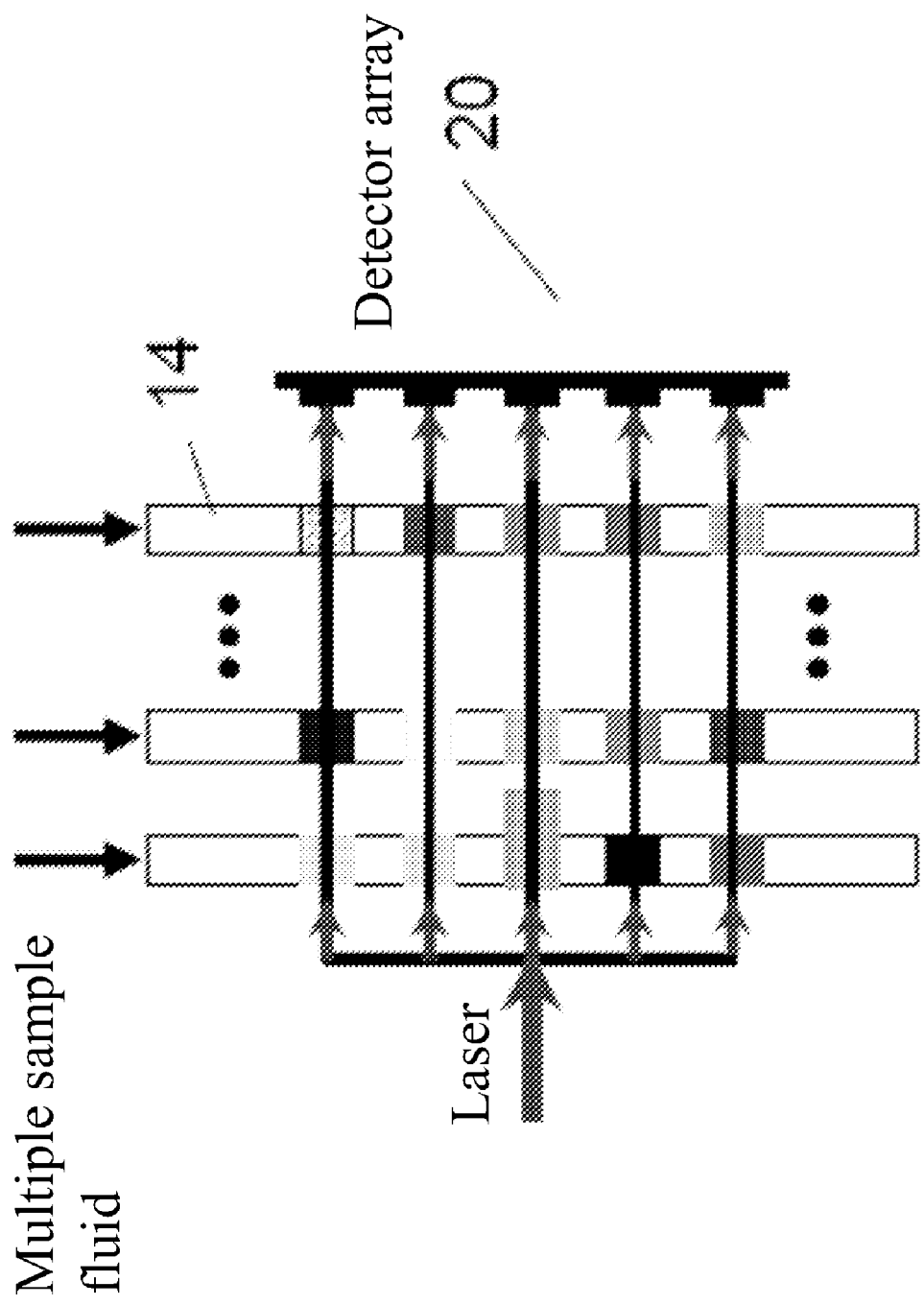
FIGS. 6(A) & (B) depict the schematics of HCORR sensor arrays.

In the transverse arrangement embodiment, the HCORRs are capable of establishing a sample detection array, as shown in FIG. 6(A) and may be further integrated into a 2-D array for simultaneous analysis of multiple samples, as shown in FIG. 6(B). In the transverse arrangement, the WGM of each constituent ring resonator is launched through horizontally arranged optical fiber tapers while the aqueous samples are conducted by the vertically positioned hollow-core capillaries. FIGS. 6(A) and (B) depict the schematics of HCORR sensor arrays with several hollow-core capillaries (14) arranged parallel to each other, where a 1-D detector array (20) is employed in FIG. 6(A) and a 2-D detector array (22) is placed above the sensor array in FIG. 6(B). The latter design fully utilizes all available spaces, i.e., light delivery, fluid delivery, and transduction signal delivery will be engineered and manipulated in all three dimensions independently. In particular, ring resonator sensors may be tracked by their spatial location. Moreover, data acquisition can be carried out by spectral imaging techniques, allowing a user to process a large amount of data in a parallel manner.

In an array format, the HCORR possesses large sensing capability and sample analysis power. Since each ring resonator is smaller than about 1000 μm in outer diameter (preferably about 30 μm to 500 μm) and separated by less than about 100 μm along the capillary, about $10^3$ to $10^4$ sensor heads can be packed onto a 1 cm² chip. In analogy to electronic integrated circuits, assuming that the sample flow as data flow and the micro-pumps and micro-valves as the control gates to direct the data flow, each ring resonator may act as an optical processor to compute and analyze the data. Such high processor density greatly increases the functionality of lab-on-a-chip devices. Moreover, the sample volume required for detection is on the order of about 100 pL, much smaller than that required by many commercialized instruments and sensors.

For the WGM to have sufficient exposure to the core for sensing applications, the wall of a HCORR sensor is preferably to be on the order of microns in thickness (ranging from about 1 μm to about 20 μm), more preferably ranging from about 1 μm to about 10 μm, and even more preferably from about 2 μm to about 5 μm. The inner and outer surfaces must be very smooth to avoid excessive scattering of the resonating light. In addition to circular/elliptical shape, a HCORR may also assume the shape of a polygon or an elliptical shape. Additionally, the HCORR sensor may be comprised of many optical materials, including but not limited to glass (e.g. quartz, fused silica, borosilicate, etc.), polymer materials that are transparent in the visible or near infrared (e.g. PDMS), semiconductor materials that are transparent in the visible or near infrared (e.g. GaAs, InGaAs, etc.), or other dielectric materials.

Although temperature may sometimes impact the performance of label-free optical sensors, it is not considered to be a significant drawback to the HCORR. For an HCORR, it is preferable to precisely determine its WGM spectral position, as it is directly related to the HCORR detection limit. However, temperature fluctuations may minimally deteriorate the HCORR sensing capability by adding noise to the WGM spectral position. For a thick-walled HCORR, the amount of the light in the core is negligible. When the HCORR wall becomes thinner, the evanescent field of the WGM in the core increases, and, and the possibility of noise should be considered. However, since the thermo-optic coefficient for the core, which is typically water (or other organic solutions), is negative and large in magnitude in comparison with that for the wall, the thermal noise is generally subdued and may be considered inconsequential. Our experiments further show that at certain wall thickness, the water effect will completely counterbalance the thermal noise induced by the wall, leading to elimination of the thermal noise to the first order.

Similarly, the WGM spectral position of an LCORR may potentially be susceptible to the variation in the differential pressure between the liquid in the core and the surrounding medium (e.g., atmosphere). Generally, the Q-factor for an LCORR is on the order of $10^6$. In order to keep the pressure induced noise small in comparison with the spectral resolution set by the WGM spectral linewidth (or the Q-factor), restrictions on the external pressure that pushes the liquid sample through the LCORR and on the flow rate may need to be imposed, especially when mechanical pumps such as peristaltic pumps are used. For example, if the Q-factor is $10^6$ and if we assume that the spectral resolution is one hundredth of the WGM spectral linewidth, then the variation in differential pressure should be kept below 10 Pa.

With respect to mode extension, the HCORR spatial resolution along its axis is on the order of 10-100 μm, which is important in HCORR capillary electrophoresis and chromatography for high resolution on-column detection. As a result, the cross-talk between the adjacent ring resonators can be significantly reduced, if the separation of these resonators is larger than 100 μm.

The present invention marks the first attempt to solve the photonic and fluidic integration problem by using the hollow core concept. The many unique features of the HCORR allow one of skill in the art to separately engineer the photonics and fluidics. The HCORR may also be used to provide dual use of the ring resonator as a sensor head and as a fluidic cell. In such an embodiment, no additional fluidic cell is required. Moreover, in the transverse arrangement, scale-up to a 2-dimensional HCORR array can readily be accomplished. All these features significantly simplify the processes in sensor miniaturization and multiplexing. In addition, the volume of the fluidic cell, the minimum volume needed for detection, may be less than 0.1 nL, which is hundreds of times smaller than in commercialized sensor instruments. Furthermore, the unique architecture of the HCORR solves the problem of interference between the light delivery and the sample delivery, which has drastically compromised the performance of ring resonator sensors in the past. Furthermore, the structure of the HCORR advantageously prevents light leakage from occurring, which is critical to maintaining the integrity of quantitative assays. The HCORR is capable of performing label-free, fluorescence-labeled, and Raman based detection. As such, the HCORR architecture may be utilized in sensor arrays for detection of various bio/chemical analytes.

Despite the small physical size of the HCORR and sub-nanoliter sensing volume, the effective interaction length can exceed 10 cm due to high Q-factor, significantly improving the HCORR detection limit. The HCORR is a versatile system that exhibits excellent fluid handling capability inherent to capillaries and is capable of non-invasive and quantitative measurement at any location along the capillary. Furthermore, the HCORR may use the refractive index change as a transduction signal, which enables label-free detection. Therefore, the HCORR is a promising technology platform for future sensitive, miniaturized, lab-on-a-chip type sensors.

The HCORR may employ a micro-sized glass capillary whose circular cross section forms ring resonators. The sample passes through the HCORR capillary while waveguides arranged perpendicularly to the capillaries deliver light, which couples into the HCORR wall evanescently. In this aspect, the HCORR relies on the presence of the evanescent field of the WGM in the core to interact with the sample passing through the capillary. The HCORR architecture achieves dual use of the capillary as a sensor head and as a fluidic channel. As a result, the HCORR retains the meritorious high sensitivity and small sample volume of ring resonators while exhibiting the excellent fluid handling capability inherent to capillaries.

The HCORR design is scalable to a 2-dimensional array for high throughput detection with each capillary being patterned with different biorecognition molecules. It is estimated that ideally $10^3$ to $10^4$ sensor heads (ring resonators) may be packed onto a 1 cm$^2$ chip. This arrangement enables multi-analyte detection and minimizes false positives by building in redundancies. Furthermore, for a 1 cm long, 50 μm diameter HCORR, the total sample volume may be only 20 nano-liters, with an average of 200 pico-liters (pL) for each ring on the HCORR, assuming that each ring is 100 μm apart along the HCORR. Like other ring resonator sensors, the HCORR is capable of performing label-free measurements. The binding of biomolecules to the HCORR interior surface or the bulk solution change results in a modification in the effective refractive index experienced by the WGM, leading to a change in the WGM spectral position.

Capillary electrophoresis may also be combined with the HCORR device. In this manner, the HCORR achieves dual use of the capillary as a sensor head and a CE fluidic channel, allowing for integrated, multiplexed, and noninvasive on-capillary detection at any location along the capillary. In this HCORR embodiment, electroosmotic flow may be used as a model system to demonstrate the fluid transport capability of the HCORR. In addition, flow speed measurements may be used to demonstrate the HCORR's flow analysis capability. Finally, using the HCORR's label-free sensing mechanism, the analyte concentration within the hollow core can be determined in real time at a given point on the capillary. Thus, the HCORR combines photonic technology with microfluidics and enables rapid on-capillary sample analysis and flow profile monitoring.

As compared to conventional microsphere, microdisk, microring based sensors in which the evanescent field outside the sphere is used for sensing, the HCORR has the following unique elements and distinguishing features: (1) ease in integrating fluidics and photonics, including the separate engineering of fluidics and photonics; (2) adaptability for scaled-up to 2-D arrays for multiplexed sensing; (3) capability for use in sensing platform for liquid samples, gaseous samples, colloidal mixtures, etc.; (4) sensing versatility as the HCORR can also be used as a pressure or temperature sensor; (5) adjustable sensitivity which is modulated by wall thickness of the optical tube (a thinner wall results in a larger evanescent field, which enables higher light-matter interaction, and thus higher sensitivity); (6) different modes allow for different penetration depth into the hollow core, which can be used to minimize noise; and (7) an extremely reduced wall thickness.

2. Fabrication of HCORR

Figure 7:
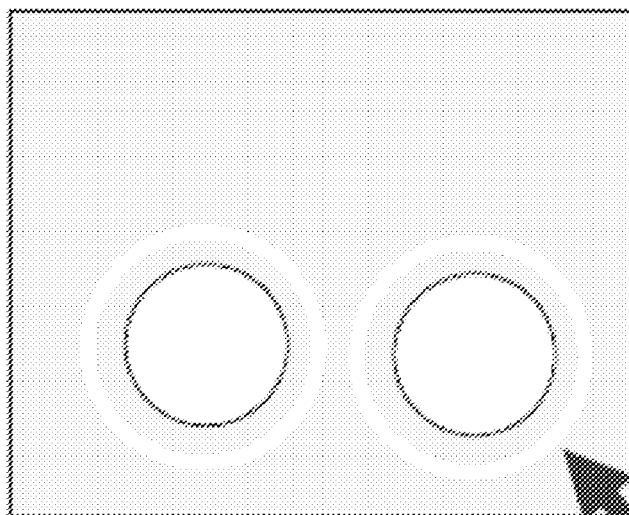
FIG. 7 shows a fabrication method for HCORR, laser ablation.
Figure 8:
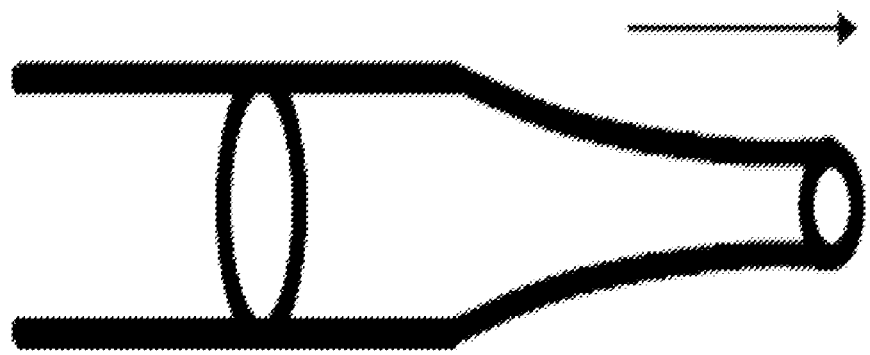
FIG. 8 shows a fabrication method for HCORR, draw tower.
Figure 9:
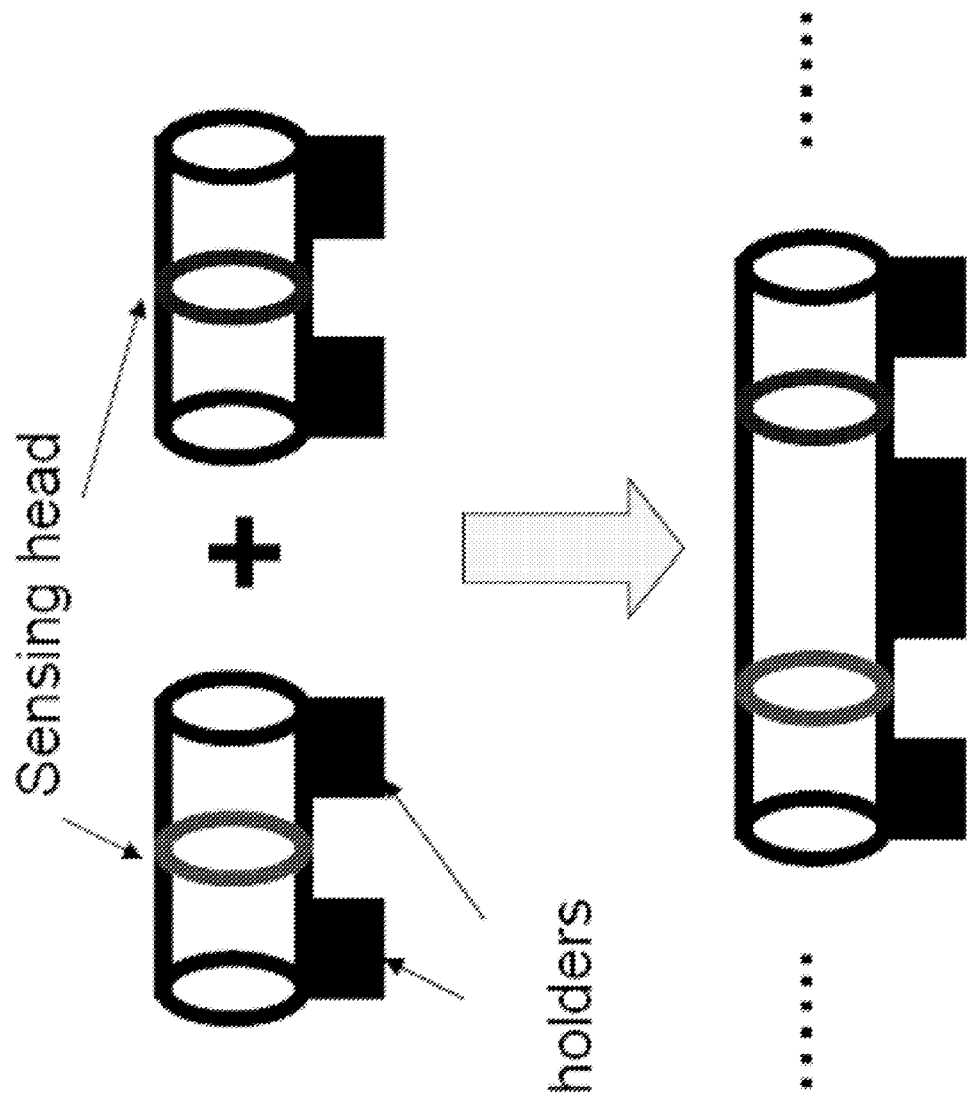
FIG. 9 shows a fabrication method for HCORR, assembly from ring resonators.
Figure 10:
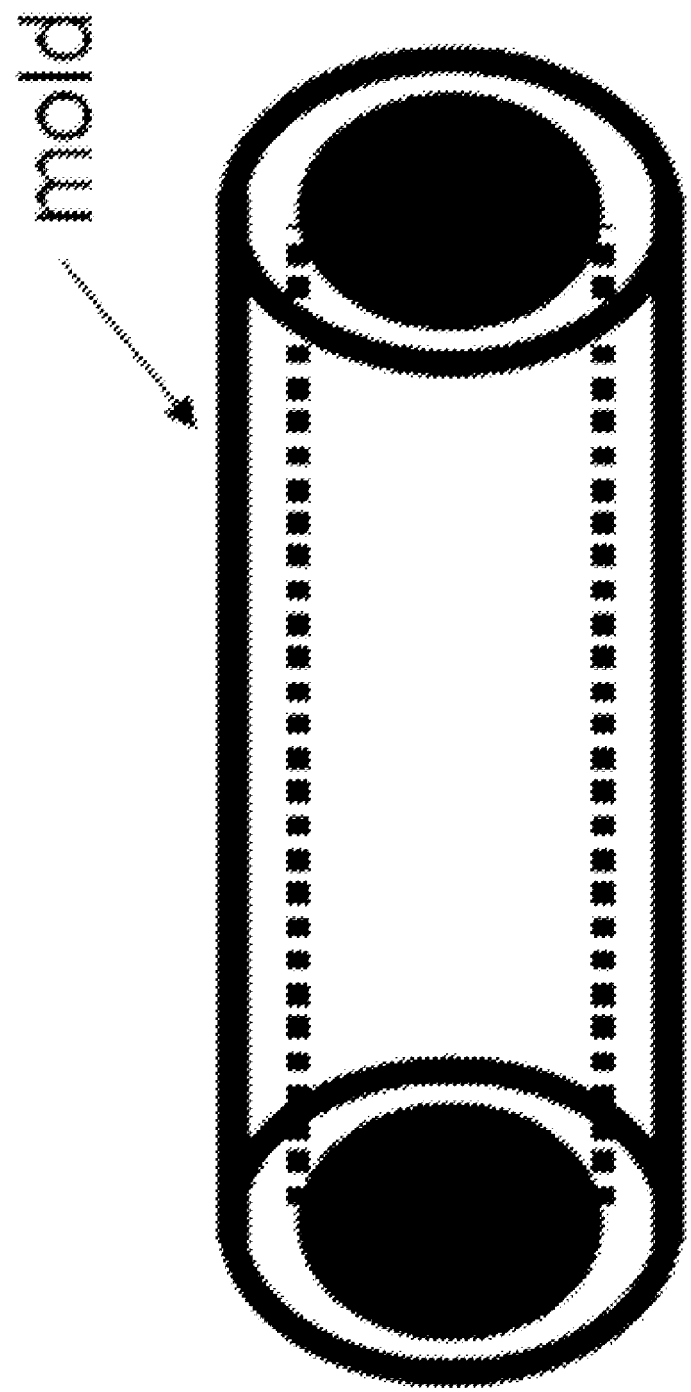
FIG. 10 shows a fabrication method for HCORR, polymer molding.
Figure 11:
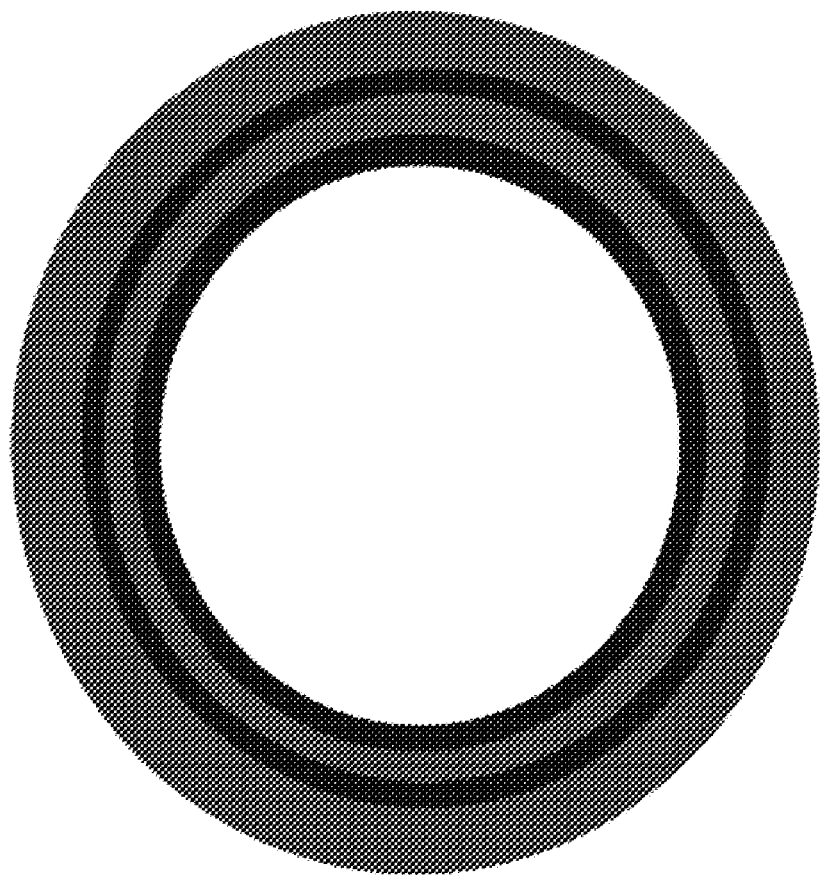
FIG. 11 shows a possible fabrication method for HCORR, photonic crystal structure, wherein top-view depicts the annular rings in alternating colors.
Figure 14A:
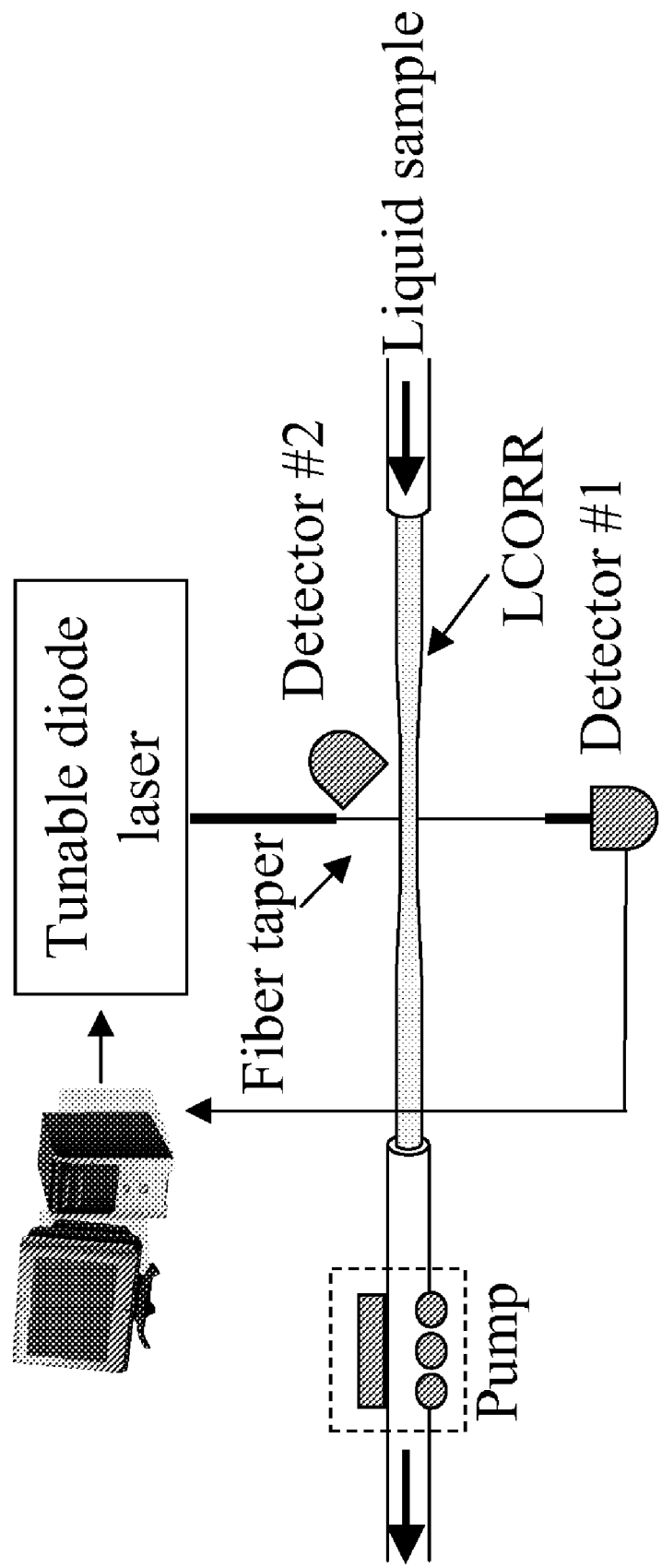
FIG. 14(A) depicts a HCORR sensing system.
Figure 14C:
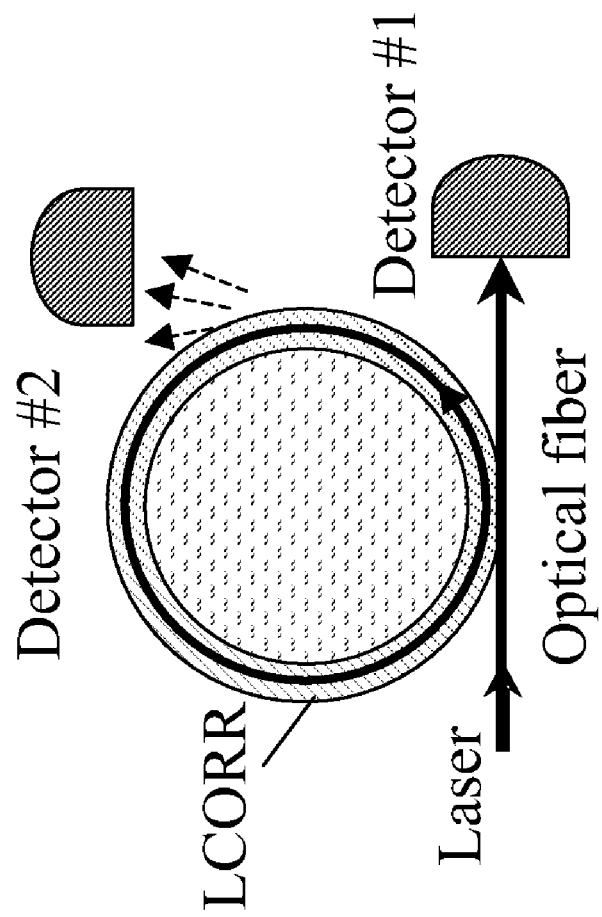
FIG. 14(C) shows the HCORR system in association with Detectors #1 and Detector #2, which are detecting optical signals form the optical fiber (input optical signal) and light emitted from the HCORR (optical output signal) respectively.
Figure 14B:
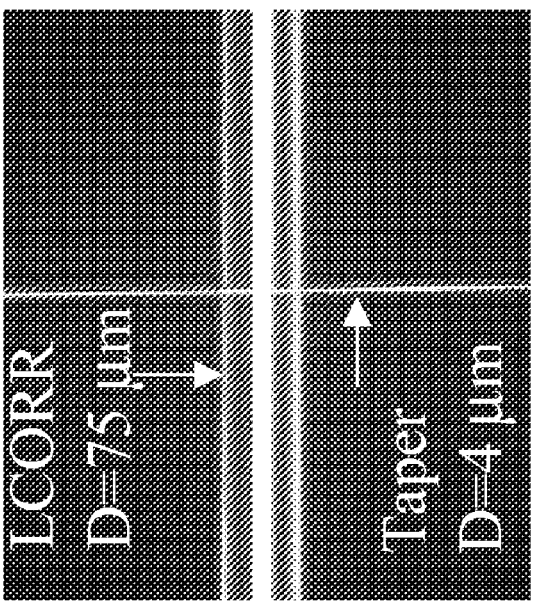
FIG. 14(B) shows the HCORR with a 75 µm outer diameter transverse to a 4 µm fiber taper.
Figure 14D:
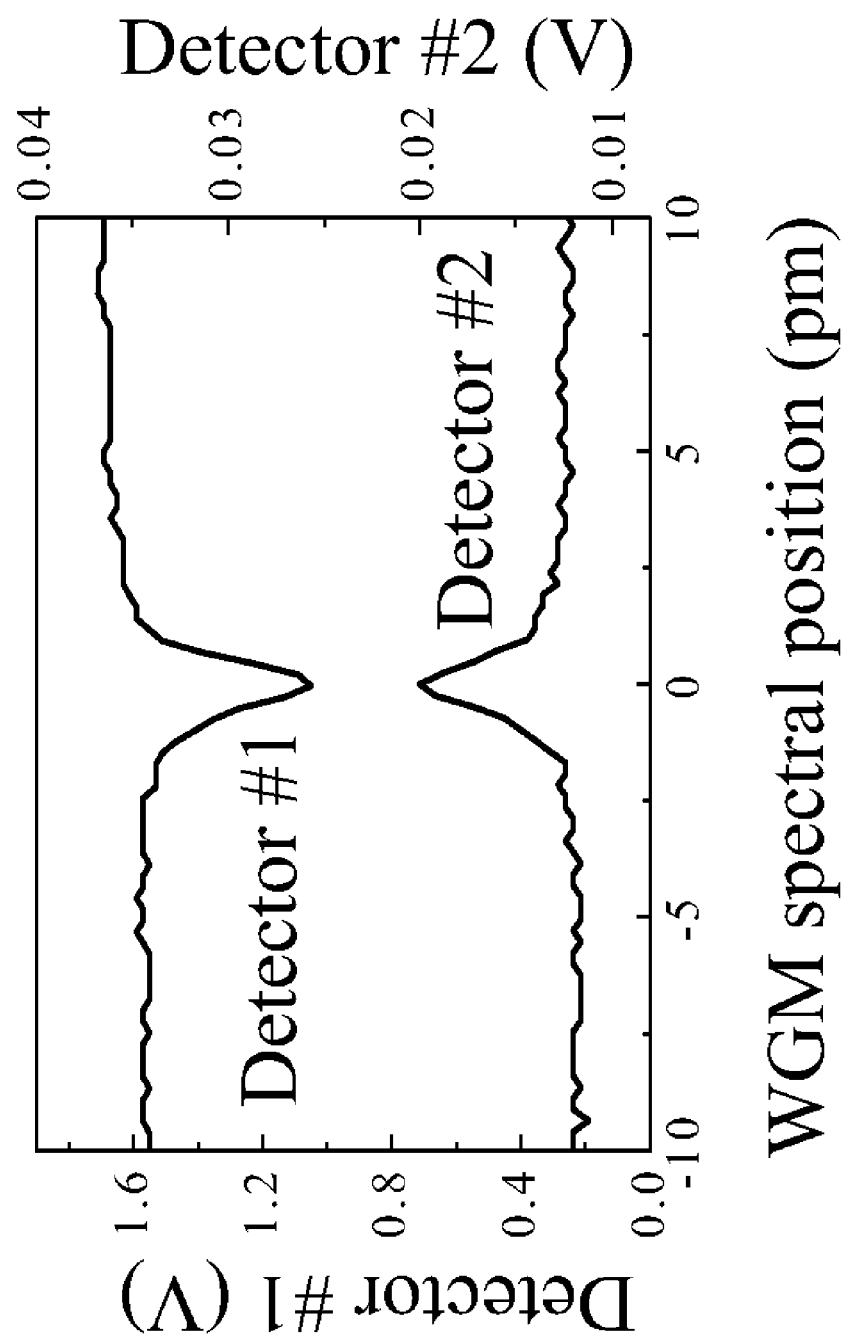
FIG. 14(D) illustrates the WGM resonance spectra of Detectors #1 and #2, which are depicted in FIGS. 14(A) and 14(C).

The invention further provides several methods of fabricating the HCORR. One possible method of fabrication is to use laser ablation to drill features such as slots or holes on a piece of optical material, as shown in FIG. 7. A second possible method is to use lithographic technology to fabricate vertical capillaries with predetermined dimensions, such as the outer and inner diameters. A third possible method is to use an apparatus such as a draw tower to pull a glass tube to fabricate capillaries with predetermined dimensions, as shown in FIG. 8. A fourth possible method is assembling/fusing individual rings, i.e., ring resonators, into a capillary-like tube, as illustrated in FIG. 9. A fifth possible method is using polymer molding, as illustrated in FIG. 10, where a pre-selected optical polymer is injected into a pre-constructed mold and cured thereafter to form HCORRs. A sixth possible method is to employ photonic crystal structures to form HCORRs, as shown in FIG. 11 with multiple annular layers alternated with different crystal materials. Yet, another possible method is to selectively etch the sacrificial layer of a cylindrical optical material, as shown in FIG. 12.

The HCORR may also be produced by a method comprising the following steps:
(a) mechanically pulling an optical tube under high temperature, thereby producing an optical tube with an outer diameter ranging from about 10 μm to about 1000 μm; and
(b) etching the inner or outer surface of the of the optical tube with a solution comprising acids, thereby producing a wall thickness ranging from about 1 μm to about 20 μm, wherein the active ingredients of the etching solution are determined by the compositions forming the optical tube.

In the above method, the appropriate etchant solutions are determined by the compositions making up the optical tube. For example, an etchant comprising HF may be used for an optical tube comprising glass, whereas an etchant comprising $H_2O_2/H_3PO_4$ may be selected for optical tubes comprising InGaAs. The concentration of an etching solution and the etching time period may vary according to the desired wall thickness and the optical material employed. Similarly, the high temperature described in (a) may be achieved through rapidly pulling a glass tube while heating the center section with a heating coil, a flame, or a $CO_2$ laser.

However, the preferred methods to fabricate a HCORR sensor are mechanical pulling or chemical etching, or a combination of both (with the pulling/etching combination as the most preferred) of an optical tube with hollow core to dramatically and evenly reduce its wall thickness to a few microns. While wall-thinning may be accomplished in a two-step process, mechanical pulling and chemical etching, a three-step process, which comprises the steps of pre-etching, pulling, and a post-etching, is a preferred embodiment. Specifically, one of the preferred methods for fabrication of HCORR with desired wall thickness from a cylindrical optical tube with hollow core comprises the steps: (1) pre-etching the outer surface of the tube by submerging said tube into a pre-etching solution to produce a pre-etched tube with a reduced outer diameter, (2) pulling the pre-etched tube at one or both ends, while heating the pre-etched tube to produce an elongated tube (e.g. rapidly pulling a glass tube while heating the center section with a heating coil, a flame, or a $CO_2$ laser), and (3) post-etching the elongated tube by running a post-etching solution into the hollow core of the elongated tube while monitoring the sensitivity in real time to produce the HCORR with desired wall thickness.

As mentioned above, in the aforesaid pre-etching and etching steps, the etchant (the active ingredient in the pre- and post-etching solutions) is selected according to the optical material employed. For example, HF is selected to etch any type of glass, while $H_2O_2/H_3PO_4$ is selected for InGaAs. The concentration of an etching solution and the etching time period may vary according to the desired wall thickness and the optical material employed.

In the aforesaid pulling step, a pre-etched tube is fixated at its two ends on two movable stages and at same time, heated by a heating source. Preferably, the heating source is mounted on a movable platform to ensure an even pulling. The heating process cures the outer and inner surfaces of the optical tube to achieve the required smoothness. While it is contemplated that the heating source may be of various types to suit individual applications, when a silica rod is used, a hydrogen torch is preferred.

More specifically, by controlling the ratio between the feed-in and pulling speeds, one is able to control the final size of the HCORR and its wall thickness. In practice, a certain degree of collapsing may occur due to glass surface tension, as reported in the literature on capillary pulling, leading to a thicker wall. The collapsing effect may be mitigated by using a higher pulling speed and/or lower heating temperature. After systematic investigation in pulling parameters, and quality check of the final size and the wall thickness using an optical microscope, it may be ascertained that the capillary aspect ratio (the capillary aspect ratio, i.e., $\eta=R/t$, where R is the outer radius and t is wall thickness) is maintained after pulling.

3. HCORR Sensing Applications

The invention further provides an HCORR sensor system to detect fluid samples, as illustrated in FIG. 14(*a*). The inventive HCORR sensor system comprises (a) a light source, said light source being capable of emitting light at a single or plurality wavelength(s), (b) a HCORR with a wall at a certain predetermined thickness, said light source being positioned to emit laser light toward said HCORR wall and said HCORR emitting at least a portion of said laser light therefrom, and (c) a detector detecting the light emitted from said HCORR.

Specifically, in FIG. 14(*a*), laser light emitted from the tunable laser through a fiber taper travels to HCORR perpendicular to the fiber taper. Light of resonating wavelengths couples into the WGMs of the HCORR. The remaining laser light that does not resonate continues to traverse the fiber taper, where it is detected by a photodetector. The photodetector signal is recorded by a data acquisition card (National Instruments) in a computer. During detection, a sample fluid is delivered through the hollow core of HCORR with an optional pump to aid the flow of the sample fluid. As the tunable laser scans across a fixed spectrum, dips in the photodetector signal occur when the wavelength matches the resonant condition. Specifically, the computer software used to post-process the recorded photodetector tracks the spectral position of the WGM resonance, creating a sensor signal. In an exemplary embodiment, a tunable laser (New Focus) is set at about 980 nm, and a Newport detector is employed. The fiber taper is produced by stretching a standard single mode fiber (Corning SMF28) under an $H_2O$ flame until it is about 3 μm in diameter.

Figure 15:
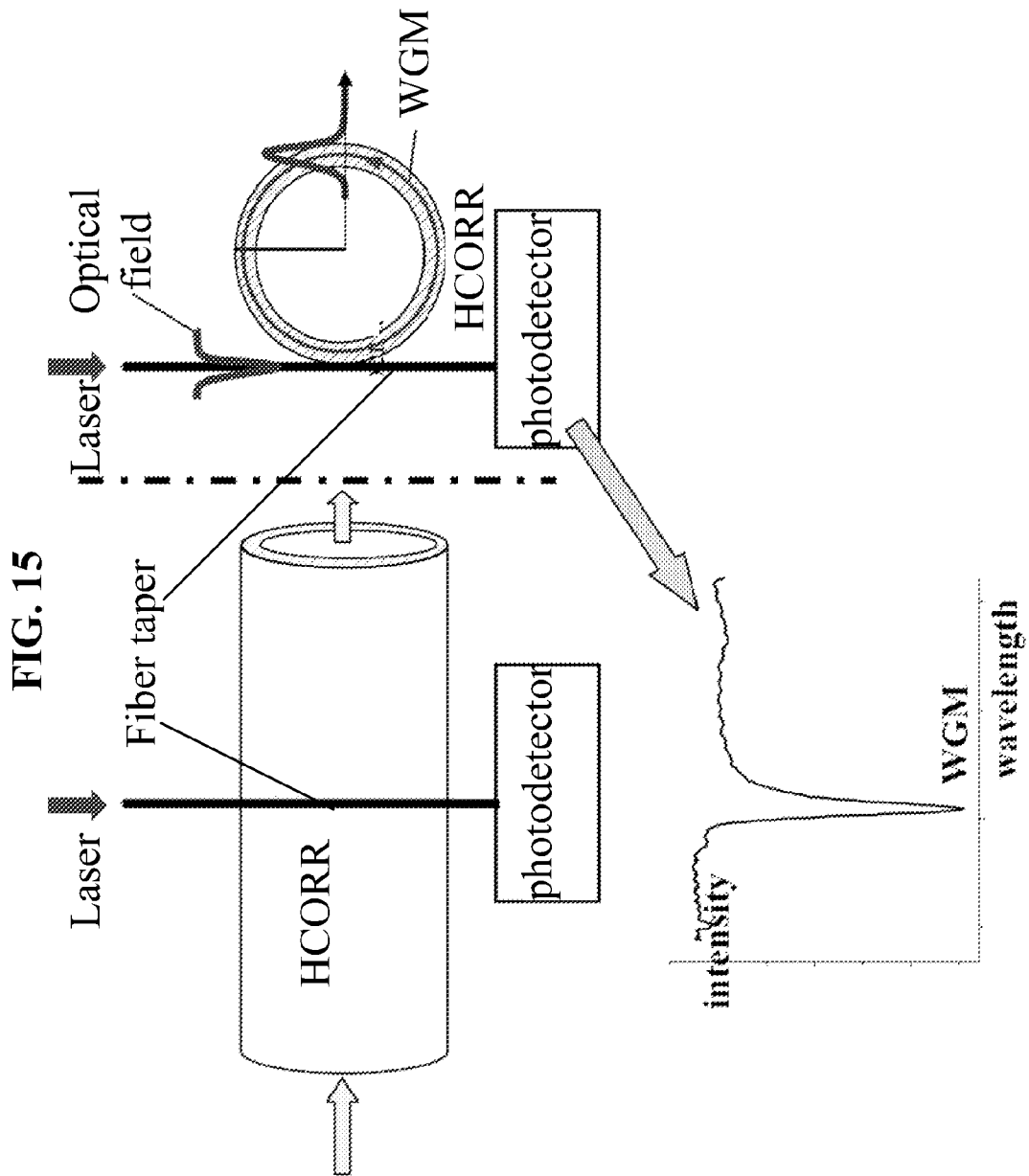
FIG. 15 illustrates a HCORR sensing mechanism.

The invention further teaches several possible sensing applications for a HCORR sensor. The basis of the sensing mechanism is illustrated in FIG. 15. When laser light passes by a HCORR sensor via a tapered fiber cable (fiber taper), an evanescent field extends beyond the fiber taper and enables the light to couple into the wall of the HCORR. The coupling light is "trapped" in the thin wall of the HCORR and repeatedly circulates, and at the same time, an evanescent field of the trapped coupling light extends into the hollow-core and interacts with analytes in a sample passing through the sensor. To avoid any potential problem in thermally induced WGM shift caused by Joule heat generated (e.g. by electro-osmotic flow (EOF)), the HCORR may be connected to a peristaltic pump for sample delivery.

Another sensing application for using the HCORR is the following. A method for detecting a target analyte comprising the following steps:

(a) guiding light of a known wavelength through an optical tube with a hollow core, thereby producing an associated evanescent field which is capable of extending into the hollow core, and an associated whispering gallery mode that is measurable as an optical signal output;

(b) measuring the optical signal output; and, (c) detecting the presence of a target analyte by comparing the optical signal output and the guided light input.

Figure 16:
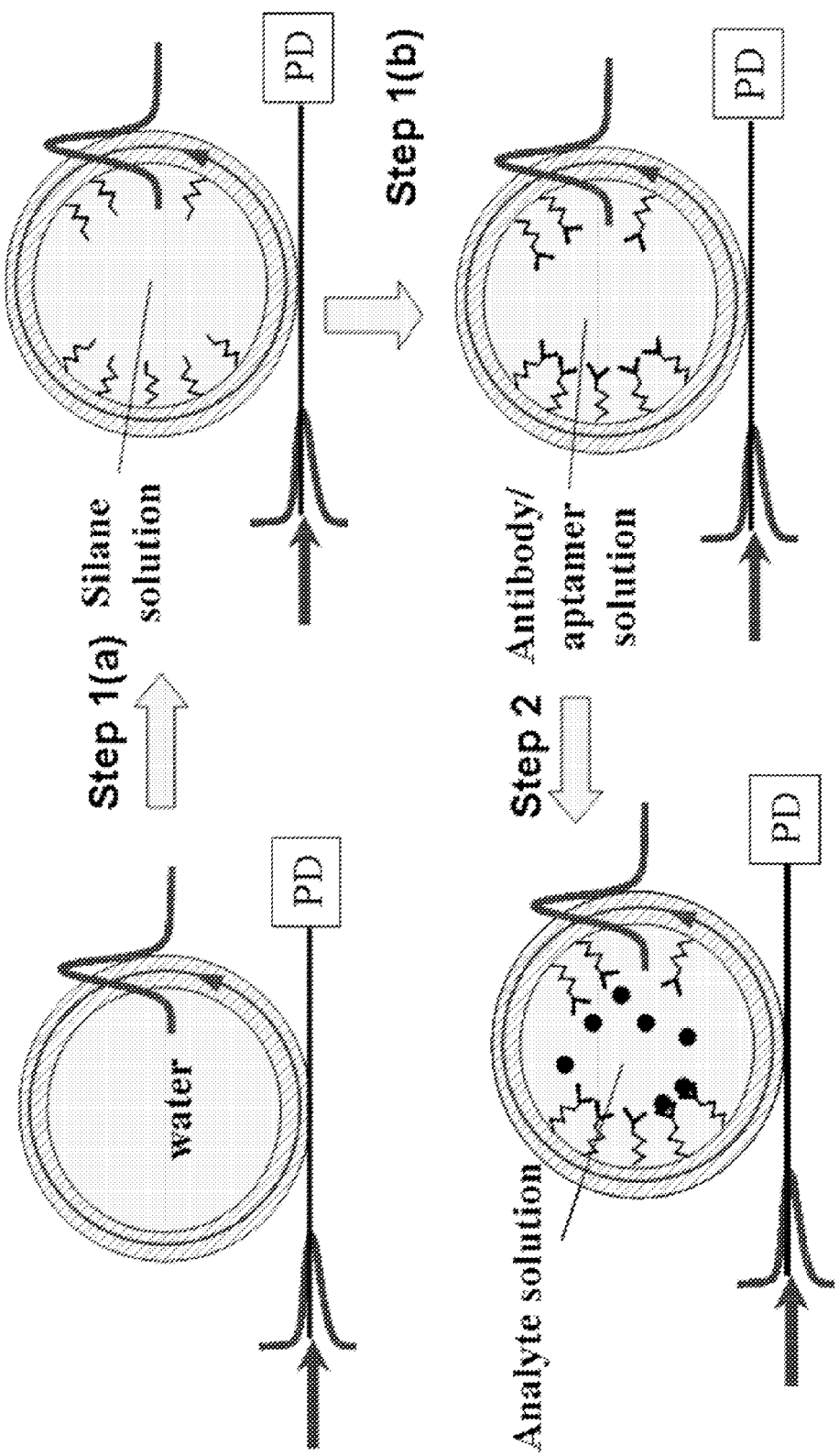
FIG. 16 provides an exemplary application of HCORR label free sensing, wherein a silane solution is passed through the fluidic channel of the HCORR and certain constituents of the solution become attached to the inner surface of the HCORR (step 1$a$) that may function as antibody/aptamer binding sites. Then an antibody/aptamer solution is passed through the same hollow core of the HCORR such that the antibodies/aptamers may become affixed to antibody/aptamer binding sites (step 1b). After that, an analyte solution is passed through the hollow core of the HCORR such that target analytes (represented as circles) may bind to the antibody/aptamers attached to the inner surface of the HCORR through the silane from the previous steps, thereby producing a an optical signal output that may be used to determine the quantity of target analyte present in the analyte solution. In this illustration, the analyte substrate comprises the silanized antibody/aptamer structures affixed to the inner surface of the HCORR.

A HCORR sensor may also achieve label-free sensing. When analytes in a sample bind to the inner surface of the HCORR during a detection, the refractive index changes, which then causes the WGM(s) to shift. This shift in spectrum may reveal quantitative and kinetic information about binding and in turn, identify the presence of the analytes. FIG. 16 provides an exemplary application of a HCORR sensor in detection of biological analytes. In the first step, the inner surface of a HCORR sensor may be functionalized by coating the inner surface with desired ligands. Inner surface functionalization may be conducted in two sub-steps: (a) treating the inner surface with a silane solution, and (b) coating the inner surface with functional ligands by running the ligands through the hollow-core of the sensor, where a certain amount of the ligands will be retained by the silane along the inner surface. In the second step, a fluid sample is delivered through the hollow core of the sensor, where the target analyte(s) will bind to the ligands; and third, detect and analyze the WGM spectrum shifts.

DEFINITIONS

Unless otherwise defined, all technical and scientific terms used herein have the same meaning as commonly understood by one of ordinary skill in the art to which this invention belongs.

The term HCORR stands for "hollow core optical ring resonator." Specifically, HCORR refers to an optical tube with a hollow core, with the optical tube having an outer diameter ranging from about 10 μm to about 1000 μm and a wall thickness ranging from about 1 μm to about 20 μm. Alternatively, HCORR is sometimes referred to as LCORR (liquid core optical ring resonator), even though the device is not limited to use with liquids.

The term "optical tube" is understood to have its ordinary meaning having a hollow core. In addition to encompassing hollow cylindrical structures (e.g. with a circular or elliptical tube shape), "optical tubes" may also be polygonal, semi-curved, substantially curved, stacked annular layers, or comprised of a plurality of fused tube-like sections. The optical tube may be made by any optical material known in the art, particularly including glass, quartz, fused silica, borosilicate, optical plastics, polymer materials, PDMS, semiconductor materials, GaAs, InGaAs, photonic crystal structures, dielectric materials, or any mixtures thereof. The optical tube may be produced by using any one of the following methods or combination thereof: laser ablation of optical materials; lithographic technology; etching, mechanical pulling; fusing ring resonators into capillary-like tubes; polymer molding; and, forming photonic crystal structures (e.g. multiple annular layers with different crystal materials).

The term "smooth" refers to the surface(s) of a ring resonator that has a Q-factor on or above the order of $10^4$.

The term "light source" refers to any form of light or optic signal that may be contacted or applied to an HCORR, thereby producing an evanescent field and whispering gallery modes within the HCORR device. The light source may be guided or unguided. One light source may be a guided light comprising a tunable laser diode passing through a fiber taper or waveguide. In particular, a light source may be capable of emitting laser light at a single or plurality of wavelength(s). Another light source may be light in a free-space coupling configuration. Light source includes free space WGM excitation, as well as free space scattering.

The term "target analyte" refers to any composition of matter known in the art that may be capable of being detected by a ring resonator (e.g. changes in optical signals caused by change in refractive index or mode). Detection by a ring resonator may be direct or indirect (e.g. binding complexes). In the event an analyte substrate is capable of being detected by a ring resonator, both the analyte substrate and the bound analyte-analyte substrate complex may also considered "target analytes." "Target analytes" include but are not limited to atoms, ions, nanoparticles, inorganic and organic compounds, molecules, macromolecules, proteins, antibodies, aptamers, antigens, nucleic acids, DNA, RNA, nucleotides, sugars, polysaccharides, carbohydrates, or any combinations thereof.

The term "analyte substrate" refers to any structure or composition of matter, which is capable of binding a target analyte. The analyte substrate may be free-floating in the hollow core of the HCORR. Alternatively, the analyte substrate may be affixed, permanently or impermanently, to the interior surface of the HCORR by any physical or chemical means known in the art. In particular, the analyte substrate may be comprised of UV-activated photosensitive molecules.

The term "fluidic channel" is defined as the void formed by the inner walls of the optical tube. The term is meant to include anywhere within the interior of the fluidic channel such that an analyte substrate may be free floating, as well as include the surface where the fluidic channel meets the inner surface of the optical tube such that an analyte substrate may be affixed to the inner surface. Importantly, the term "fluidic channel" does not require fluids or liquids to be present. For instance, the fluidic channel may be dry.

The term "test sample" refers to any composition of matter comprising liquids, gases, or solids, which may be passed through the hollow core of the HCORR. Specifically, the test sample may include a target analyte.

The phrase "field is capable of interacting with test samples" refers to modulations in the optical signal of the HCORR that may occur if the test sample contains a target analyte. The interaction of the field with the test samples may be indicated by change in refractive index of the optical signal or a change in mode for the whispering gallery modes (WGMs).

EXAMPLES

Example 1

Figure 17:
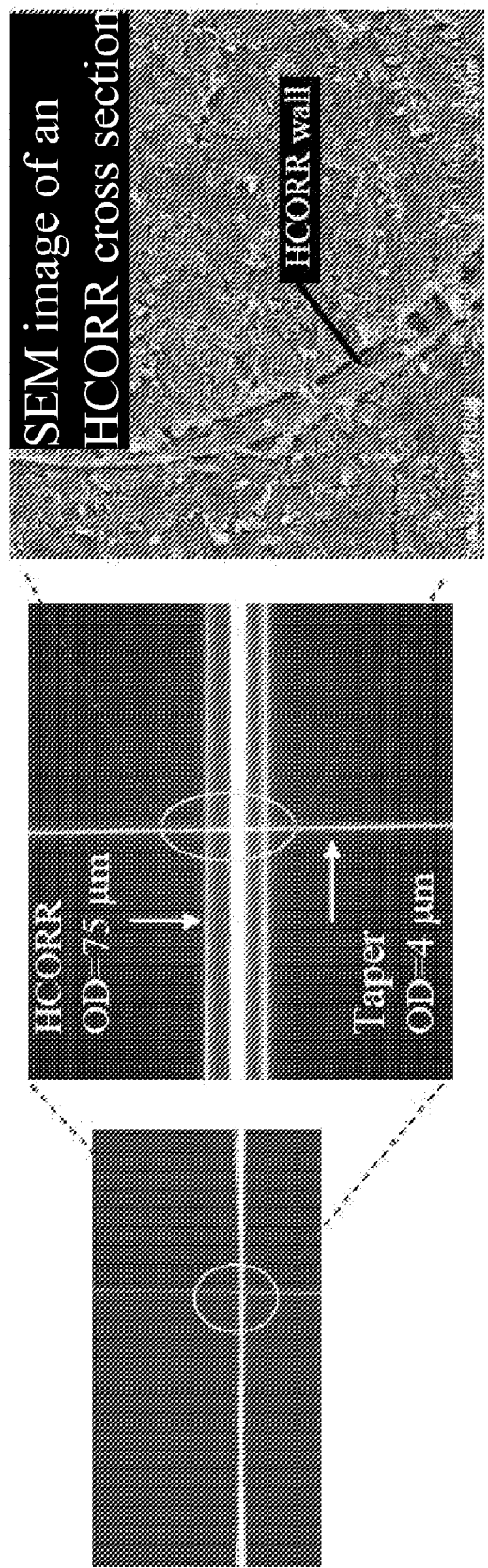
FIG. 17 shows a SEM image of a cross section of an HCORR.

The following example relates to a method of fabricating a HCORR. Specifically, an HCORR was formed by etching and pulling the center section of a fused silica capillary (r1~0.45 mm, r2~0.6 mm). The capillary was first pulled under an H$_2$O flame (using the mechanical pulling set-up illustrated in FIG. 13) until the outer radius reaches about 35-50 μm. To achieve the desired wall thickness, the elongated capillary was etched by pumping low concentrations of HF (<10%), preferably about 5% HF, through the hollow core of the capillary for a period of 30 minutes to 2 hours. After final-etching, the resulting capillary was rinsed by pumping water through its hollow core, which yielded the desired HCORR with a wall thickness of about 2 to 4 μm. FIG. 17 shows an SEM image of about one quarter of the cross section of an HCORR.

Example 2

The HCORR device described in Example 1 was tested. During the sensing application, the HCORR was positioned in contact with a fiber taper of approximately 3-4 μm in diameter to obtain a WGM spectrum. Light from a tunable laser diode (980 nm) was coupled into the WGM through the evanescent coupling at the HCORR exterior surface. The tunable laser was repeatedly scanned across a wavelength range of about 100 pm. The WGM spectral positions were recorded at the output end of the taper.

Figure 18:
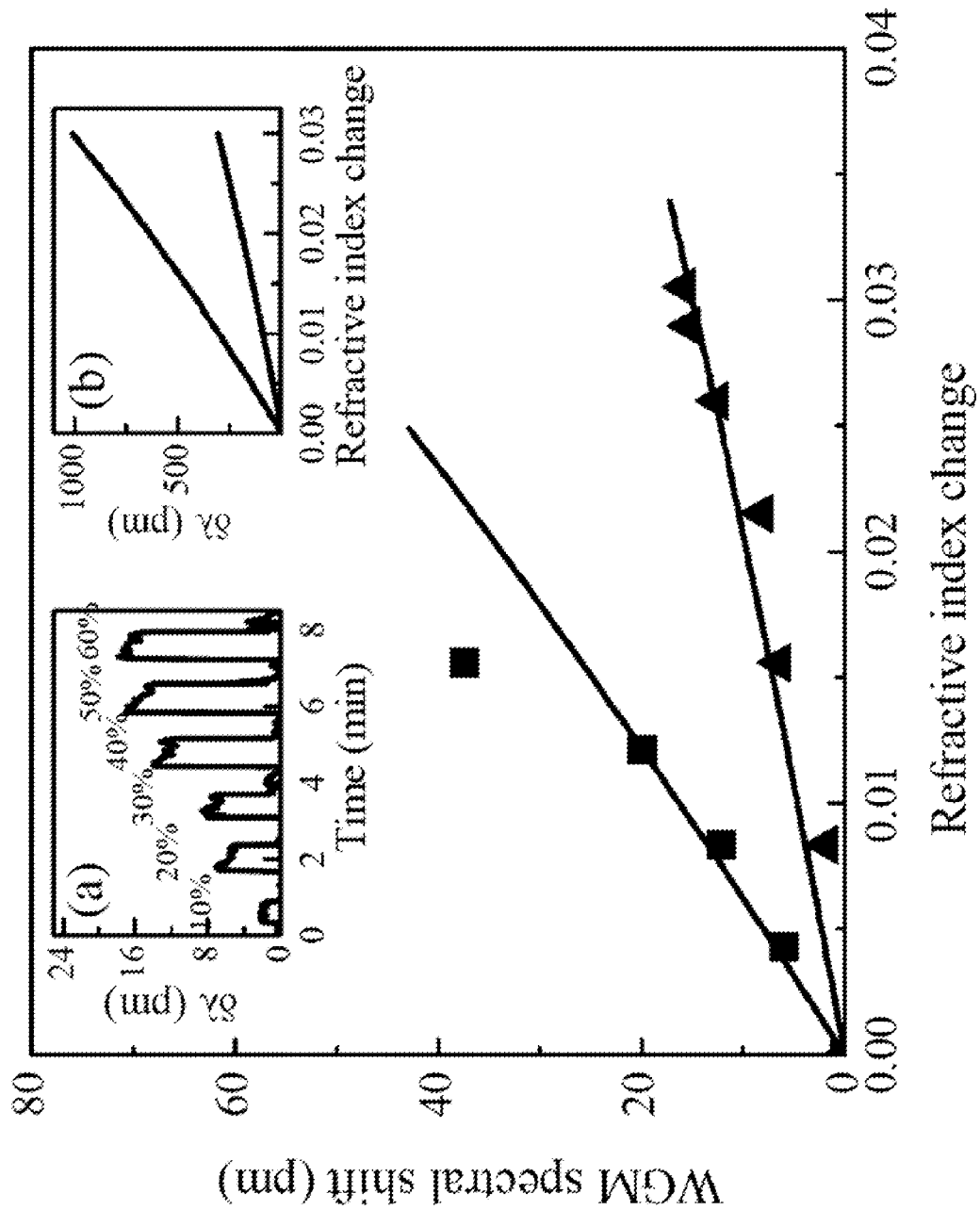
FIG. 18 shows changes in refractive index as varying concentrations of ethanol are pumped through the HCORR.

The sensing capability of a HCORR sensor has been assessed by detecting changes in refractive index when a solution of ethanol and water was delivered through the sensor's hollow core. Incremental concentrations of 10%, 20%, 30%, 40%, 50%, and 60% were pumped through the HCORR with a rinsing step between each increment to ensure that the HCORR was free of residual ethanol from the prior increment. Two exemplary HCORRs were used with wall thickness of about 3.6 μm (▲ in FIG. 18) and 3.0 μm (■ in FIG. 18), respectively. The resulting sensorgram for the HCORR with a wall thickness of 3.6 μm is given in the inset (a) in FIG. 18. The increasing red shift due to increasing concentrations can be seen clearly in the steps on the graph, which coincide with the introduction of the ethanol concentrations into the sensing system. FIG. 18 plots the spectral shifts recorded in the sensorgram against the change in refractive index units (RIU), as computed from the ethanol concentrations using the formula:

$$1.333+0.179x-0.380x^2+0.352x^3-0.125x^4$$

where x is the mole fraction of ethanol in water [15].

The sensitivities for the two exemplary sensors are approximately 500 μm/RIU and 2000 μm/RIU for the 3.6 μm and 3 μm HCORRs, respectively. The sensitivity of the HCORR is in line with a typical ring resonator sensor. However, the HCORR sensor carries a higher Q-factor than a typical ring resonator, which leads to better detection capability. The Q-factors for the two exemplary sensors are about $1.2 \times 10^6$ and $4.1 \times 10^5$ for the 3.6 μm and 3 μm HCORRs, respectively.

Example 3

Figure 19:
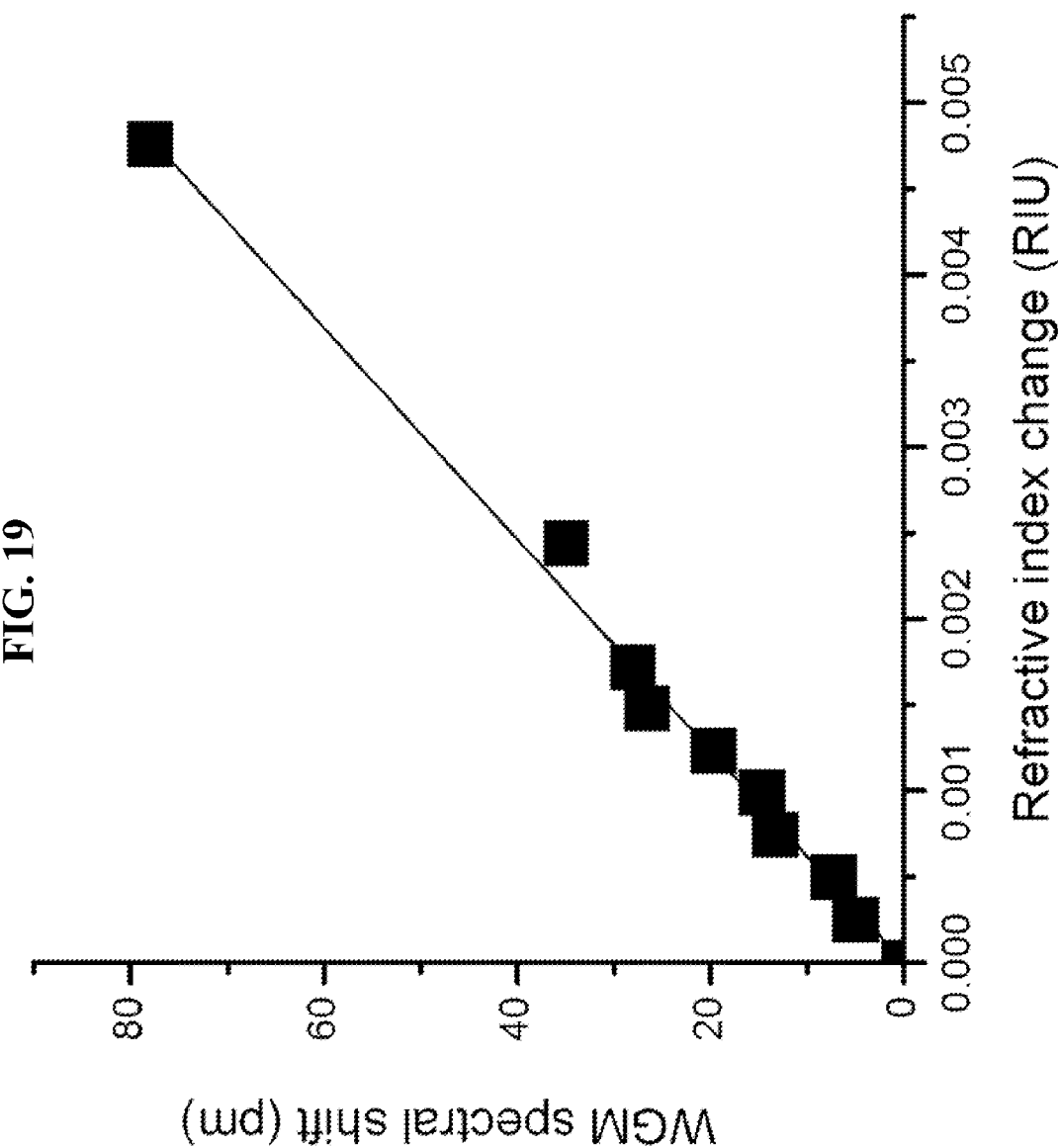
FIG. 19 shows changes in refractive index as varying concentrations of methanol are pumped through the HCORR.
Figure 20:
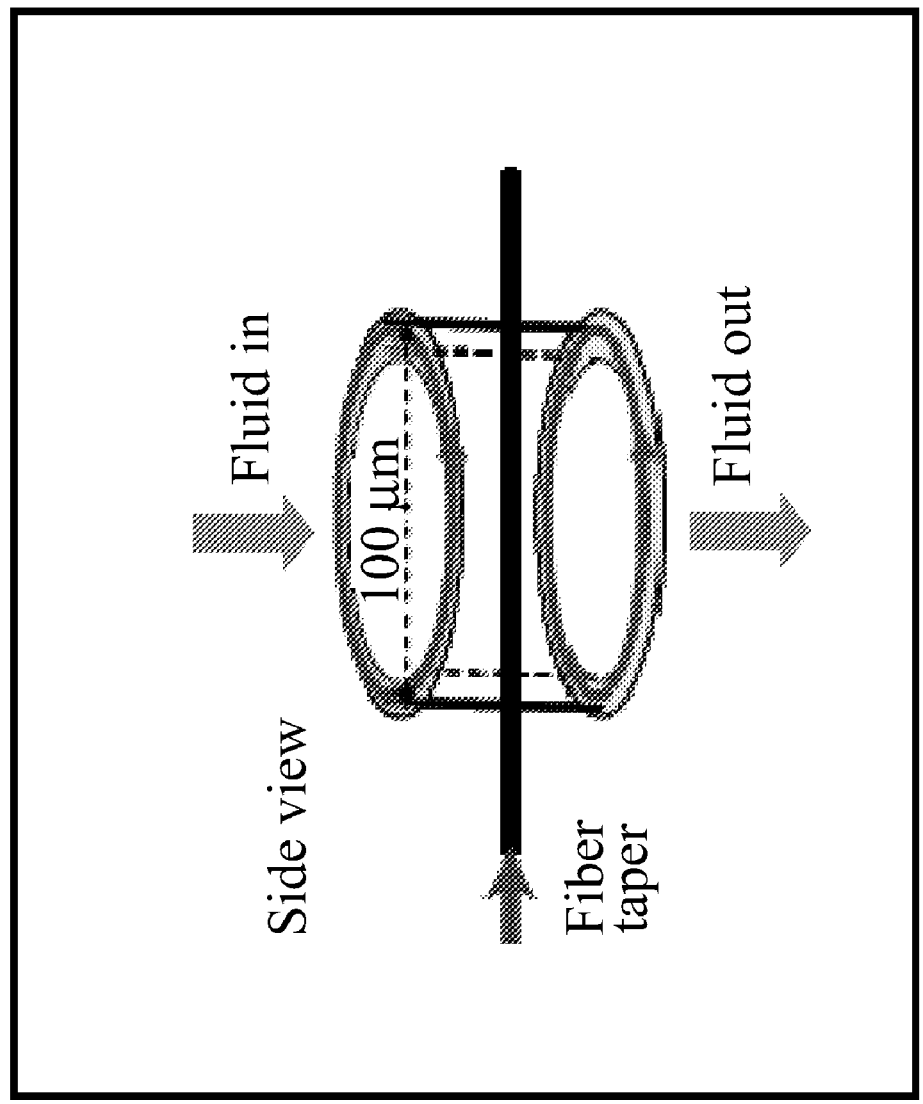
FIG. 20 shows a conceptual side-view illustration of a proposed embodiment of the HCORR horizontally (i.e. transverse arrangement).
Figure 21:
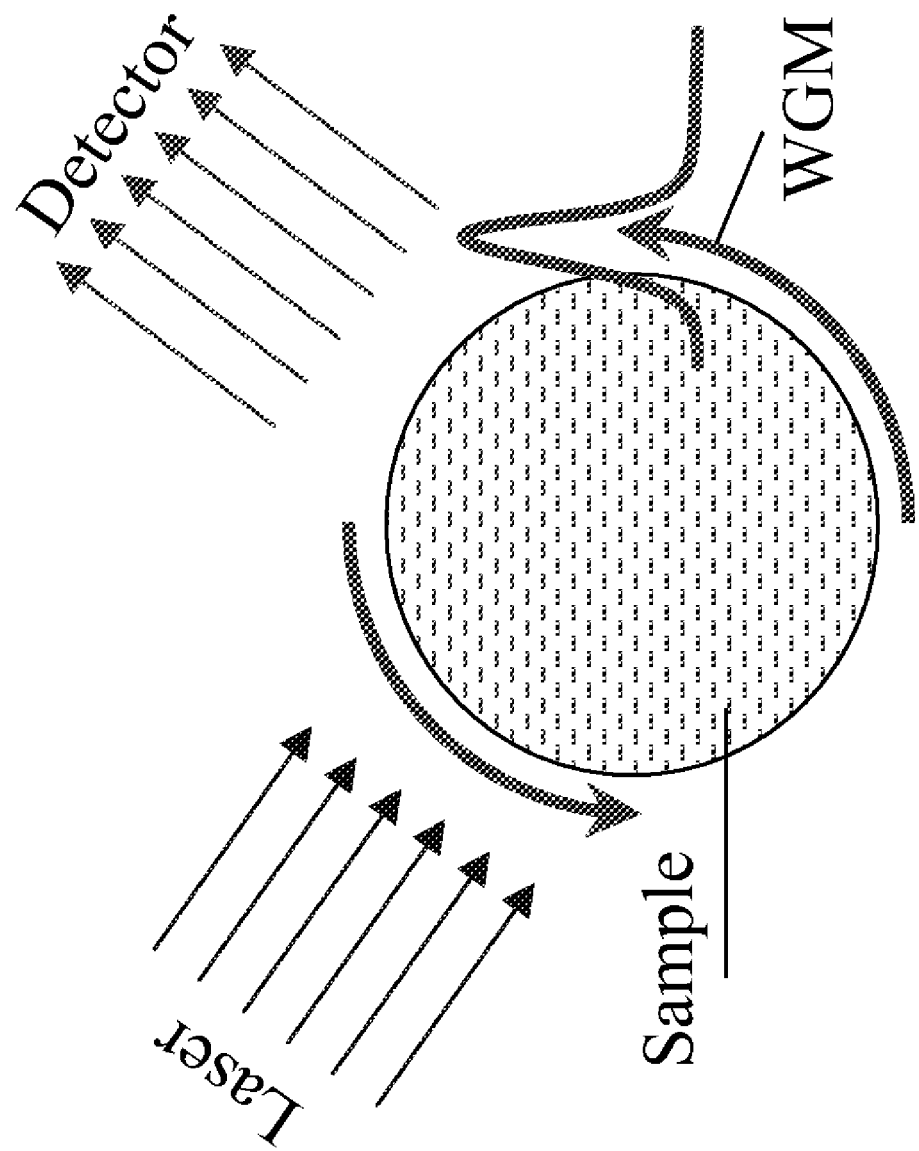
FIG. 21 shows a free-space light source (laser) producing WGMs within the HCORR filled with a sample, whereby the HCORR then emits some portion of the light as a light output signal toward a detector.

In addition to the tests described above (ethanol and water), the HCORR device described in Example 1 was also tested on additional target analytes including methanol. In particular, the HCORR sensor has also been employed to detect changes in methanol concentration based on the changes in refractive index when a solution of methanol and water was delivered through the sensor's hollow core. Incremental concentrations of methanol (1%, 2%, 3%, 4%, 5%, 6%, 7%, 10%, 20% v/v in water) were pumped through the HCORR with an outer diameter of about 80 μm and a wall thickness of approximately 2 μm. A rinsing step between each increment was conducted to ensure that the HCORR was free of residual methanol from the prior increment. The result is shown in FIG. 19.

While the invention has been described in connection with specific embodiments thereof, it will be understood that the inventive method is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

Example 4

The following example describes a method of fabricating an HCORR. The HCORR may be a piece of a fused silica hollow tube of 50-100 micron in OD (outer diameter), with a wall thickness approximately 1-5 microns. The HCORR may be fabricated by pulling a fused silica hollow tube with a much larger OD (typically 1 mm) under high temperature. The light may be coupled into the HCORR through a fiber taper and circulates along the wall of HCORR. This circulation mode of the light is called the whispering gallery mode (WGM). WGM has an evanescent field extended into the surrounding media on both interior and exterior sides of the HCORR wall. Therefore, the WGM is sensitive to any change occurring on or in close proximity of the wall. The HCORR may be used either in the presence or in the absence of liquid samples. When the liquid sample is used, the liquid sample is conducted by the hollow core of the HCORR. Once the sample reaches the section where there is a WGM mode, the WGM interacts with the sample and sensing transduction signal will be detected by a detector (or detector array) through the fiber taper, or through another light guiding systems. In addition to liquid samples, samples in gaseous state may also be guided through the hollow core. Bodily fluids such as blood or urine may also be used as test samples and guided through the hollow core. Furthermore, the HCORR may also be used as a sensor in response to the refractive index or/and shape change in the HCORR induced by such factor as pressure and temperature.

Example 5

The following example describes a method of fabricating an HCORR. In one manner of producing the HCORR, the wall thickness of the optical tube may be approximately 5 μm in order to have a sufficient evanescent field on the interior surface. To achieve this, fused silica micropipettes (Sutter Instrument) with an inner diameter (ID) of 900 μm and an outer diameter (OD) of 1200 μm are utilized. The pipette will be placed on a computer-controlled pulling station (which we built for fabrication of optical fiber tapers), heated with either a CO$_2$ laser or a H$_2$O torch, and stretched gradually (~15 μm/s) from both ends. Studies have shown that all features on the pipette cross section will shrink proportionately. Therefore, when a 5 μm thick wall is achieved, the ID of the LCORR is expected to be 30 μm. In the event that the final column ID might be too small to permit easy conduction of sample fluid, an alternative method of production involves pre-etching the pipettes with buffered HF solution (Sigma-Aldrich) to thin the wall from 150 μm to 30 μm. This may eventually yield a HCORR with an ID larger than 100 μm, a typical size used in most commercialized columns for liquid sample delivery. Different fabrication parameters, such as pulling speed, pulling distance, pre-etching time, will be explored to make straight and uniform-sized HCORRs. The fluidic cell volume of the HCORR, estimated from the diameter of the hollow core (~100 μm) and the extension of the WGM along the axial direction (<10 μm), is on the order of 0.1 nL.

Example 6

The following example describes a method of testing an HCORR. Various tests may be performed on the HCORRs to characterize their mechanical and optical properties. It is important to find out whether the mechanical strength of an HCORR may withstand the water pressure necessary to push the sample through the HCORR. For this purpose, a peristaltic pump may be used at various flow rates. Typically a flow rate of a few tens of μL/min is sufficient for most applications. Then the Q-factor of the HCORR will be measured by placing the LCORR against an optical fiber taper. A Q-factor on the order of $10^6$ is expected based on our previous studies on microsphere ring resonators. Although HF etching will certainly introduce significant amount of roughness on the micropipette surface that spoils the Q-factor, subsequent pulling under extremely high temperature (>fused silica annealing point) will cause the silica to reflow, thus smoothing the surface.

The next step will be to characterize the evanescent field strength on the HCORR interior surface—the part of the WGM responsible for the interaction with captured molecules. This may be done by filling the hollow core with various refractive index matching fluids (Cargille) (1.333-1.45) while monitoring the WGM spectra position and power at the output end of the fiber taper. With the increased refractive index at the core, the WGM is gradually "pulled" towards the center, leaving the evanescent field at the exterior surface decoupled from the fiber taper. The onset of this decoupling depends on the wall thickness or the evanescent field strength. The thicker the wall is, the lower the evanescent field strength is, and hence the higher refractive index onset. To verify and guide the experiment, a theoretical model based on Mie theory may be constructed to calculate the radial distribution of the WGM under different conditions such as HCORR size, wall thickness, and the refractive index of the core. The target evanescent field strength on the interior wall may be set to 1-5% of the WGM peak intensity.

The HCORR's refractometric sensitivity may impact the analyte detection limit of the optical sensor. The sensitivity curve may be obtained from the WGM spectral shift as a function of the refractive index change in the core. For this purpose, a modification in the refractive index as low as 10-4 may be needed, which can not be achieved with Cargille fluids. This may be accomplished through an injection of an ethanol-water mixture of different concentrations into the column. Using this method, the refractive index may be adjusted from 1.333 to 1.36 with the desired resolution.

Example 7

The following example describes a method of using an HCORR as a sensor. A biotin-conjugated Bovine Serum Albumin (BSA) and Streptavidin may be used in combination as a model system to investigate the sensing feasibility of HCORRs. The interior surface of the HCORR may be activated for bioconjugation using one of three approaches. The simplest approach is oxygen plasma activation, in which the HCORRs are placed in the plasma chamber for a few minutes. One concern, however, is that the efficiency of plasma activation may be low due to the small opening in the HCORR. If this problem arises, one may use either piranha (two parts of $H_2SO_4$ and one part of $H_2O_2$) or UV ozone treatment to circumvent the problem. These two approaches require slightly longer time. Then, the HCORR interior surface will be silanized to introduce functional groups, followed by incubation in 1 mg/mL biotin-BSA solution for 1 hour. Streptavidin, known to have strong affinity towards biotin, will subsequently be injected at various concentrations through the peristaltic pump.

The WGM spectral position is monitored and correlated with the Streptavidin concentrations. The sensor results will be compared with those obtained with the conventional sensor configuration in which the evanescent field on the exterior surface of a ring resonator is employed. The HCORR sensitivity may then be optimized by varying wall thickness and column ID under the guidance of the theoretical model constructed previously, and then utilize the HCORR for actual bio/chemical sensing applications.

Example 8

The following example describes a method of using an HCORR as a sensor. Biorecognition molecules, such as antibodies, may be immobilized onto the interior surface of the HCORR. The evanescent field of the guided light in the HCORR may extend into the hollow core (e.g., aqueous test sample) for approximately 100 nm and interact with the biomolecules near the interior surface of the HCORR. A small change in refractive index near the interior surface when target analytes are captured causes modifications in the optical signal (such as phase) at the output, which acts as the sensing signal. Since the sensing signal is accumulative in nature, a longer light-analyte interaction length results in a lower detection limit. Advantageously, in an optical ring resonator such as an HCORR, the light propagates in the form of whispering gallery modes (WGMs), which result from the total internal reflection of the light along the curved surface. The WGM is a surface mode, and it circulates along the resonator surface and interacts repeatedly with the analytes on its surface through the WGM evanescent field.

A more generalized way of characterizing the HCORR as a sensor is the following. A method for using the HCORR as a sensor comprising the following steps:

(a) coating the interior surface of the HCORR with a analyte substrate that is capable of binding a target analyte or molecule of interest;

(b) associating a light source with the HCORR, wherein an optical signal comprising an evanescent filed and whispering gallery modes are produced within the optical tube of the HCORR;

(c) detecting the optical signal for a control value through a photodetector in contact with the optical signal of the HCORR;

(d) measuring the control value of the optical signal through a data acquisition card on a computer that is in communication with the photodetector;

(e) contacting the interior surface of the HCORR with a test sample comprising a liquid, gas, solid, or some combination thereof, wherein a target analyte may be present;

(f) measuring the optical signal for a test value associated with the test sample, wherein modulations to the optical signal may be caused by the presence of a target analyte within the test sample;

(g) repeating steps (c)-(d) for the test value; and (h) subtracting the control value from the test value to determine the normalized test value, thereby determining whether a target analyte is present in the test sample.

As compared to a straight waveguide sensor, the effective light-analyte interaction length of a ring resonator sensor is no longer determined by the sensor's physical size, but rather by the number of revolutions of the light supported by the resonator, which is characterized by the resonator quality factor, or the Q-factor. Thus, by directly or indirectly monitoring the WGM spectral shift, it is possible to obtain both quantitative and kinetic information about the binding of molecules near the surface. This label-free sensing mechanism allows for the detection of biomolecules in their natural form without the laborious fluorescent labeling process, as well as the detection of non-fluorescent chemical molecules.

Example 9

The following example describes a method of using an HCORR as a sensor. The WGM spectral position can be obtained as a function of wall thickness, the HCORR size, operating wavelength, etc., which allows one to calculate the HCORR sensitivity to bulk refractive index change and to optimize the HCORR design. For the HCORR with the radius much larger than wavelength, the WGM spectral position can be approximated by using the following equation in which WGM spectral position, i.e., resonant wavelength, $\lambda$, is related to the refractive index through the resonant condition: $\lambda = r\ n_{eff}\ \pi/m$, where r is the ring outer radius, neff is the effective refractive index experienced by the WGM, and m is an integer that describes the WGM angular momentum. In this equation, neff is determined by the refractive index of the core (sample), capillary wall, and the surrounding medium (e.g., air). The listed equation significantly simplifies the relationship among the WGM spectral position, refractive index, and the HCORR radius, based on which many theoretical analyses can be performed in a very straightforward and insightful manner.

The three-layer model may further be generalized to include the analyte layer on the inner HCORR wall, and the layer thickness may be utilized to quantify the amount of biomolecules on the surface and the refractive index to describe different types of biomolecules. This embodiment provides a model for the spectral shift due to analyte deposition on the inner surface. Following this, one may determine the shift due to a single analyte molecule, assuming that each molecule is independent and non-interacting, and contributes equally to the spectral shift. This model may easily be extended to include more analyte layers to describe more complicated bio-detection processes.

Example 10

The following example describes a method of using an HCORR as a multiplex device including capillary electrophoresis. The HCORR architecture may be used for the dual use of the capillary as a sensor head and a capillary electrophoresis (CE) fluidic channel, allowing for integrated, multiplexed, and noninvasive on-capillary detection at any location along the capillary. Generally, one may use electroosmotic flow and glycerol as a model system to demonstrate the fluid transport capability of the HCORRs. In addition, the HCORR may be further utilized for flow analysis capability. Using the HCORR's label-free sensing mechanism, we accurately deduced the analyte concentration in real time at a given point on the capillary. A sensitivity of 20 nm/RIU (refractive index units) was observed, leading to an RI detection limit of 10-6 RIU. As such, the HCORR marries photonic technology with microfluidics and enables rapid on-capillary sample analysis and flow profile monitoring.

In order to utilize the HCORR as an CE fluidic device, one may use two HCORRs of 115-μm (HCORR no. 1) and 130-μm (HCORR no. 2) o.d. with a length of 2 cm in the experiment. In our experiments, each HCORR was connected to two sample reservoirs (9 mm in diameter and 5 mm in height) through UV-curable adhesives. Next, two hundred volts from a high-voltage source from Spellman (New York, N.Y.) may be placed across the HCORR, resulting in an electric field of 100 V/cm. A digital ammeter from Omega (Stamford, Conn.) was used to monitor the current passing through the HCORR. An optical fiber taper with a diameter of 3 μm, fabricated by stretching a single-mode optical fiber under flame, was brought in contact with the LCORR to couple the light from a 980-nm, tunable diode laser from New Focus (San Jose, Calif.; spectral line width <0.001 pm; repeatability <0.003 pm) into the WGM.

Two approaches were developed to detect the WGM spectral position. In the first approach, a photodetector was used to monitor the light at the terminal end of the optical fiber, whereas in the second approach, a photodetector was placed above the HCORR. In both approaches, the laser periodically scanned in wavelength at a constant power. When the laser wavelength matches the WGM resonance condition, the light couples into the ring resonator and causes the measured transmission power to drop, leaving a spectral dip at detector no. 1. In the The light coupled into the HCORR is scattered off the HCORR surface and may be detected as a spectral peak by detector no. 2. Both the measured signals can be used to indicate the WGM spectral position, which shifts in response to the RI change in the HCORR core. The first approach is easy to implement, and the second scheme is more suitable when multiple HCORRs are used for high-throughput HCORR CE development.

In our experiment, since we used only one HCORR as a model system, only detector no. 1 was employed. The laser scanning rate was 5 Hz with a scanning range of 100 pm; the output power was 1-2 mW. The entire measurement system was controlled by a computer through a data acquisition card from National Instruments (Austin, Tex.). The output power at detector no. 1 for each scan was recorded for post-analysis using in-house spectral dip detection software. A thermal shield was used to reduce the temperature fluctuation induced by air convection.

Example 11

The following example describes a method of using an HCORR as a sensor. Quantitative analysis with the HCORR: In addition to providing a transport mechanism for the sample, the HCORR is capable of on-capillary quantitative sample analysis. To demonstrate this, different concentrations of glycerol were passed through HCORR no. 2 while the WGM spectral position was monitored. First, 200 μL of buffer was added to the cathode reservoir and 150 μL of 0.001 M Na2HPO4 buffer was added to the anode. After establishing the baseline, 50 μL of glycerol was injected into the reservoir at the anode. The glycerol mixture was subsequently driven through the HCORR after 200 V was applied, causing the WGM to shift.

After each run, the HCORR was cleaned by driving the glycerol completely out of the LCORR. Then, the reservoirs were cleaned and filled with fresh buffer, and an increased concentration of glycerol was added to repeat the above experiment. During the experiment, the liquid level on the anode side was kept the same as or slightly lower than that on the cathode side to avoid any pressure-driven flow. Given the observed value of the WGM spectral shift, one can deduce the RI change and, thus, the glycerol concentration in the capillary. The RI changes were first calculated using the sensitivity of 20 nm/RIU, and the corresponding glycerol concentrations were then obtained using the glycerol calibration curve. Comparison between the deduced and the actual glycerol concentrations provided a good agreement, attesting to the quantitative analysis capability of the HCORR.

Example 12

The following example describes a method of fabricating an HCORR. An alternative method to fabricate an HCORR involves starting with a glass tube with OD=1.2 mm, ID=0.9 mm, and $\eta=4$. To increase $\eta$ (the capillary aspect ratio, i.e., $\eta=R/t$, where R is the outer radius and t is wall thickness), we pre-etch the glass tubes from outside to reduce the wall thickness by placing them in a hydrofluoric acid (HF) bath. Although pre-etching takes nearly 1.5 hours, tens of glass tubes can be batch-processed simultaneously and stored for later use. After pre-etching, the wall thickness can be reduced down to 75 µm, hence $\eta=7$. After pulling, the HCORR OD becomes 100 µm, and wall thickness is approximately 7-8 µm. To further reduce the wall thickness to below 4 µm, a diluted concentration of HF (<1%) is pumped through the HCORR to slightly etch the HCORR interior wall. This etching process is well controlled and takes approximately 20-60 minutes. When the desired wall thickness is reached, pure water is pumped through the HCORR to terminate the etching process. One apparent concern of fabricating HCORRs with such a high aspect ratio is mechanical robustness. Accordingly, we have conducted a number of experiments with HCORRs that have wall thickness of around 2-4 µm.

The HCORRs have demonstrated high mechanical integrity and may even sustain high pressure when fluid is conducted via a mechanical pump. Further improvement can be made on our current setup. First, it is highly desirable to directly obtain a wall thickness of 2-4 µm without time-consuming HF post-etching, which may also degrade the Q-factor due to the surface roughness introduced during the etching process. To achieve further reduction in the wall thickness to the perform, more HF pre-etching may be needed. Second, while our current setup may produce HCORRs of fairly uniform size, a laser micrometer may be implemented to characterize the HCORR size in-situ and in real-time, which may provide feedback for a better quality control in HCORR fabrication. It is expected that our system will produce HCORRs of tens of centimeters in length with uniform quality, which can further be diced into shorter pieces for sensor arrays.

Example 13

The following example describes a method of using an HCORR as a sensor. An alternative embodiment for an HCORR sensor includes the sample being driven into the HCORR with a peristaltic pump. Light from a tunable laser diode (external cavity laser from New Focus or DFB laser from JDSU) is coupled into the WGM through the evanescent coupling by an optical fiber taper or a waveguide in contact with the HCORR exterior surface. The tunable laser periodically scans across a wavelength range of about 100 pm while Detector #1 at the output of the waveguide or fiber taper measures the optical power. When the laser wavelength matches the WGM resonant condition, the light couples into the ring resonator and causes the measured transmission power to drop, leaving a spectral dip at Detector #1. During that time, the light coupled into the HCORR is scattered off the HCORR surface and can be detected as a spectral peak with a detector placed above the HCORR (Detector #2). Both of the measured signals can be used to indicate the WGM spectral position. The first scheme (Detector #1) is easy to implement and the second scheme (Detector #2) is more suitable when multiple HCORRs are used for high-throughput analysis. The WGM shifts in response to the refractive index change near the HCORR interior surface resulting from the capture of target molecules on the inner HCORR surface. (See, generally, FIG. 14A-D).

Figure 2A:
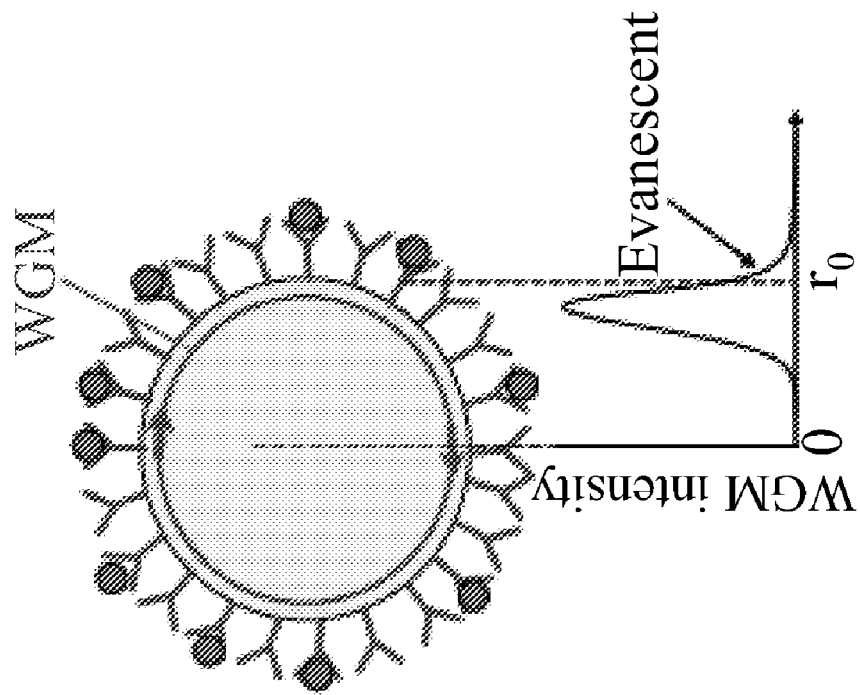
FIGS. 2(A) & (B) illustrate the general mechanism of the optical ring resonator sensors.
Figure 2B:
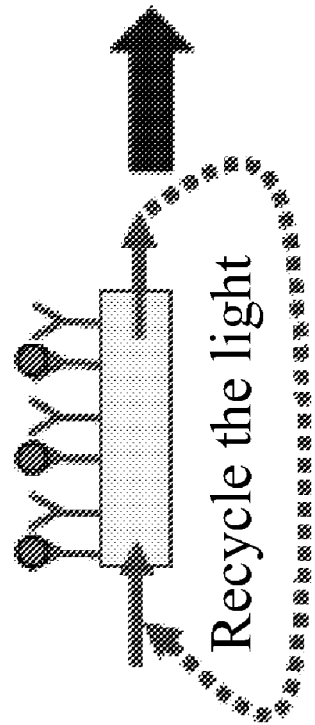
Figure 3A:
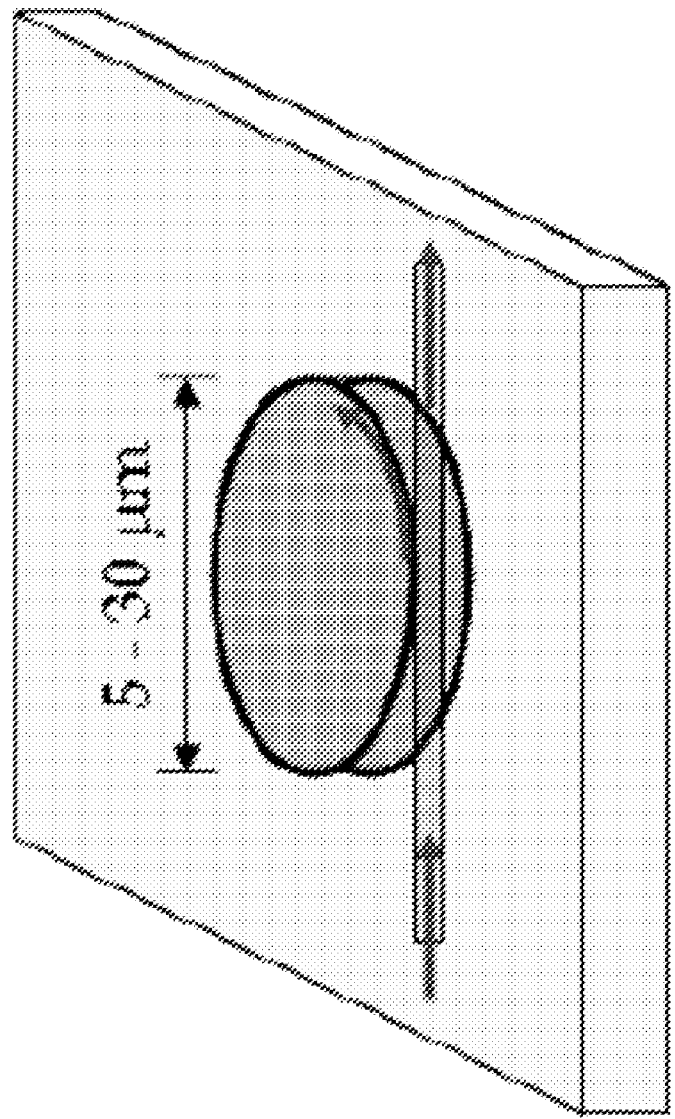
FIGS. 3(A) & (B) illustrate some examples of optical ring resonators.

A data acquisition card is used in conjunction with a computer to record the signal from the detector. The sensorgram can subsequently be obtained when the WGM position is plotted as a function of time, as shown in FIG. 2. The advantage of this approach is that it is direct and simple to implement. It has a large dynamic range (limited only by the laser scanning range) and signal linearity. Additionally, it can handle multiple ring resonator sensors, as each ring resonator may not have exactly the same WGM position. The drawback is the data acquisition rate, as a large set of data needs to be acquired and saved. In our experiment, up to 10 Hz of scanning rate is used. Although the current scanning rate may go even higher, it is adequate for most of applications in bio/chemical sensing. An alternative and indirect approach may also be exploited by fixing the laser spectral position to match half of the peak WGM intensity, and then monitoring the laser transmission intensity.

Example 14

The following example describes a method of using an HCORR as a sensor. In order to immobilize multiple biorecognition molecules such as antibody or aptamer on an LCORR, one may use a photo-assisted molecular grafting method. The inner surface of the LCORR is first silanized with thiol or amine functional groups, then a photo-sensitive cross-linker such as N-5-Azido-2-nitrobenzoyloxysuccinimide in solution is introduced, followed by exposure to a UV lamp or high intensity Argon laser through a photo-mask. Finally, the biorecognition molecule is introduced and immobilized at the exposed locations. Multiple exposures can be repeated to immobilize different types of biorecognition molecules. The HCORR is then contacted with a light source and the resulting optical signals (input and output signals) of the HCORR are detected and measured in order to quantify the presence of biomolecules within the HCORR.

While the invention has been explained in relation to exemplary embodiments, it is to be understood that various modifications thereof will become apparent to those skilled in the art upon reading the description. Therefore, it is to be understood that the invention disclosed herein is intended to cover such modifications as fall within the scope of the appended claims.

REFERENCES

[1] See, for example, *Optical Sensors*, Eds. R. Narayanaswamy and O. S. Wolfbeis (Springer, New York, 2004).

[2] L. M. Lechuga, A. T. M. Lenferink, R. P. H. Kooyman, and J. Greve, "Feasibility of evanescent wave interferometer immunosensors for pesticide detection: chemical aspects," Sensors and Actuators B 24-25, 762 (1995).

[3] C. R. Layers, K. Itoh, S. C. Wu, M. Murabayashi, I. Mauchline, G. Stewart, and T. Stout, "Planar optical waveguides for sensing applications," Sensors and Actuators B 69, 85 (2000).

[4] See, for example, *Optical Processes in Microcavities*, Eds. R. Chang and A. Campillo (World Scientific Pub Co Inc., Singapore, 1996).

[5] M. L. Gorodetsky, A. A. Savchenkov, and V. S. Ilchenko, "Ultimate Q of optical microsphere resonators," Opt. Lett. 21, 453 (1996).

[6] J. L. Nadeau, V. S. Iltchenko, D. Kossakovski, G. H. Bearman, and L. Maleki, "High-Q whispering-gallery mode sensor in liquids," in *Laser Resonators and Beam Control* V, A. V. Kudryashov, ed., Proc. SPIE 4629, 172 (2002).

[7] F. Vollmer, D. Braun, and A. Libchaber, M. Khoshsima, I. Teraoka, and S. Arnold "Protein detection by optical shift of a resonant microcavity," Appl. Phys. Lett. 80, 4057 (2002).

[8] S. Arnold, M. Khoshsima, I. Teraoka, S. Holler, and F. Vollmer, "Shift of whispering-gallery modes in microspheres by protein adsorption," Opt. Lett. 28, 272 (2003).

[9] F. Vollmer, S. Arnold, D. Braun, I. Teraoka, and A. Libchaber, "Multiplexed DNA quantification by spectroscopic shift of two microsphere cavities," Biophys. J. 85, 1974 (2003).

[10] "Biophotonics/Optical Interconnects and VLSI Photonics/WBM Microcavities," 2004 *Digest of the LEOS Summer Topical Meeting*, IEEE, Piscataway, N.J., 2004.

[11] N. M. Hanumegowda, C. J. Stica, B. C. Patel, I. M. White, and X. Fan, "Refractometric sensors based on microsphere resonators," Appl. Phys. Lett. 87, 201107 (2005).

[12] N. M. Hanumegowda, I. M. White, H. Oveys, and X. Fan, "Label-free protease sensors based on optical microsphere resonators," Sensor Lett. 3, 315 (2005).

[13] Ian M. White, Niranjan M. Hanumegowda, and Xudong Fan, "Sub-Femtomole Detection of Small Molecules with Microsphere Sensors," Opt. Lett. 30, 3189 (2005).

[14] C. F. Bohren and D. R. Huffman, *Absorption and Scattering of Light by Small Particles* (John Wiley & Sons, Inc, New York, 1998).

[15] A. A. Ghoreyshi, F. A. Farhadpour, M. Soltanieh, and A. Bansal, "Transport of small polar molecules across nonporous polymeric membranes," J. Membrane Sci. 211, 193 (2003).

[16] A. Serpenguzel, S. Arnold, and G. Griffel, "Excitation of resonances of microspheres on an optical fiber," Opt. Lett., 20, 654-656, 1995.

[17] I. Teraoka, S. Arnold, and F. Vollmer, "Perturbation approach to resonance shifts of whispering-gallery modes in a dielectric microsphere as a probe of a surrounding medium," J. Opt. Soc. Am. B, 20, 1937-1947, 2003.

[18] M. Noto, M. Khoshsima, D. Keng, I. Teraoka, V. Kolchenko, and S. Arnold, "Molecular weight dependence of a whispering gallery mode biosensor," Appl. Phys. Lett., 87, 223901, 2005.

[19] M. Noto, F. Vollmer, D. Keng, I. Teraoka, and S. Arnold, "Nanolayer characterization through wavelength multiplexing of a microsphere resonator," Opt. Lett., 30, 510-512, 2005.

[20] I. Teraoka and S. Arnold, "Theory of resonance shifts in TE and TM whispering gallery modes by nonradial perturbations for sensing applications," J. Op. Soc. Am. B, 23, 1381-1389, 2006.

[21] I. Teraoka and S. Arnold, "Enhancing the sensitivity of a whispering-gallery mode microsphere sensor by a high-refractive-index surface layer," J. Op. Soc. Am. B, 23, 1434-1441, 2006.

[22] X. Fan, P. Palinginis, S. Lacey, H. Wang, and M. C. Lonergan, "Coupling semiconductor nanocrystals to a fused-silica microsphere: a quantum-dot microcavity with extremely high Q factors," Opt. Lett., 25, 1600-1602, 2000.

[23] I. M. White and X. Fan, "Demonstration of composite microsphere cavity and surface enhanced raman spectroscopy for improved sensitivity," Chemical and Biological Sensors for Industrial and Environmental Security, Proc. SPIE 5994, 59940G, 2005.

[24] I. M. White, N. M. Hanumegowda, H. Oveys, and X. Fan, "Tuning whispering gallery modes in optical microspheres with chemical etching," Opt. Express, 13, 10754-10759, 2005.

[25] N. M. Hanumegowda, I. M. White, and X. Fan, "Aqueous mercuric ion detection with microsphere optical ring resonator sensors," Sens. Actuators B, 120, 207-212, 2006.

[26] I. M. White, H. Oveys, and X. Fan, "Increasing the Enhancement of SERS with Dielectric Microsphere Resonators," Spectroscopy, April, 2006.

[27] H. Zhu, J. D. Suter, I. M. White, and X. Fan, "Aptamer Based Microsphere Biosensor for Thrombin Detection," Sensors, 6, 785-795, 2006.

[28] J. P. Rezac and A. T. Rosenberger, "Locking a microsphere whispering-gallery mode to a laser," Opt. Express, 8, 605-610, 2001.

[29] A. M. Armani and K. J. Vahala, "Heavy water detection using ultra-high-Q microcavities," Opt. Lett., 31, 1896-1898, 2006.

[30] H. Quan and Z. Guo, "Simulation of whispering-gallery-mode resonance shifts for optical miniature biosensors," Journal of Quantitative Spectroscopy & Radiative Transfer, 93, 231-243, 2005.

[31] C.-Y. Chao and L. J. Guo, "Biochemical sensors based on polymer microrings with sharp asymmetrical resonance," Appl. Phys. Lett., 83, 1527-1529, 2003.

[32] C.-Y. Chao, W. Fung, and L. J. Guo, "Polymer microring resonators for biochemical sensing applications," IEEE J. Sel. Top. Quantum Electron., 12, 134-142, 2006.

[33] J. Yang and L. J. Guo, "Optical sensors based on active microcavities," IEEE J. Sel. Top. Quantum Electron., 12, 143-147, 2006.

[34] A. Yalcin, K. C. Popat, O. C. Aldridge, T. A. Desai, J. Hryniewicz, N. Chbouki, B. E. Little, O. King, V. Van, S. Chu, D. Gill, M. Anthes-Washburn, M. S. Unlu, and B. B. Goldberg, "Optical Sensing of Biomolecules Using Microring Resonators," IEEE J. Sel. Top. Quantum Electron., 12, 148-155, 2006.

[35] A. Ksendzov and Y. Lint, "Integrated optics ring-resonator sensors for protein detection," Opt. Lett., 30, 3344-3346, 2005.

[36] A. Ksendzov, M. L. Horner, and A. M. Manfreda, "Integrated optics ring-resonator chemical sensor with polymer transduction layer," Electron. Lett., 40, 2004.

[37] E. Krioukov, D. Klunder, A. Driessen, J. Grevea, and C. Otto, "Two-photon fluorescence excitation using an integrated optical microcavity: a promising tool for biosensing of natural chromophores," Talanta, 65, 1086-1090, 2005.

[38] E. Krioukov, J. Greve, and C. Otto, "Performance of integrated optical microcavities for refractive index and fluorescence sensing," Sens. Actuators B, 90, 58-67, 2003.

[39] E. Krioukov, D. J. W. Klunder, A. Driessen, J. Greve, and C. Otto, "Integrated optical microcavities for enhanced evanescent-wave spectroscopy," Opt. Lett., 27, 1504-1506, 2002.

[40] R. W. Boyd and J. E. Heebner, "Sensitive disk resonator photonic biosensor," Appl. Opt., 40, 5742-5747, 2001.

[41] S. Blair and Y. Chen, "Resonant-enhanced evanescent-wave fluorescence biosensing with cylindrical optical cavities," Appl. Opt., 40, 570-582, 2001.

[42] J. Scheuer, W. M. J. Green, G. A. Derose, and A. Yariv, "InGaAsP Annular Bragg Lasers: Theory, Applications, and Modal Properties," IEEE J. Quantum Electron., 11, 476-484, 2005.

[43] T. Baehr-Jones, M. Hochberg, C. Walker, and A. Scherer, "High-Q ring resonators in thin silicon-on-insulator," Appl. Phys. Lett., 85, 3346-3347, 2004.

[44] T. Baehr-Jones, M. Hochberg, C. Walker, and A. Scherer, "High-Q optical resonators in silicon-on-insulatorbased slot waveguides," Appl. Phys. Lett., 86, 081101, 2005.

[45] V. R. Almeida, Q. Xu, C. A. Barrios, and M. Lipson, "Guiding and confining light in void nanostructure," Opt. Lett., 29, 1209-1211, 2004.

[46] C. F. Bohren and D. R. Huffman, Absorption and Scattering of Light by Small Particles, John Wiley & Sons, New York, 1998.

[47] K. Vahala, Optical Microcavities, World Scientific, Singapore, 2005.

[48] J. Homola, S. S. Yee, and G. Gauglitz, "Surface plasmon resonance sensors: review," Sens. Actuators B, 54, 3-15, 1999.

[49] D. R. Reyes, D. Iossifidis, P.-A. Auroux, and A. Manz, "Micro Total Analysis Systems. 1. Introduction, Theory, and Technology," Anal. Chem., 74, 2623-2636, 2002.

[50] P.-A. Auroux, D. Iossifidis, D. R. Reyes, and A. Manz, "Micro Total Analysis Systems. 2. Analytical Standard Operations and Applications," Anal. Chem., 74, 2637-2652, 2002.

[51] P. S. Dittrich, K. Tachikawa, and A. Manz, "Micro Total Analysis Systems. Latest Advancements and Trends," Anal. Chem., 78, 3887-3908, 2006.

[52] O. Geschke, H. Klank, and P. Telleman, Microsystem Engineering of Lab-on-a-chip Devices, John Wiley & Sons, Weinheim, 2004.

[53] I. M. White, H. Oveys, and X. Fan, "Liquid Core Optical Ring Resonator Sensors," Opt. Lett., 31, 1319-1321, 2006.

[54] I. M. White, H. Oveys, X. Fan, T. L. Smith, and J. Zhang, "Integrated multiplexed biosensors based on liquid core optical ring resonators and antiresonant reflecting optical waveguides," Appl. Phys. Lett., 89, 191106-191101-191106-191103, 2006.

[55] I. M. White, H. Zhu, J. D. Suter, H. Oveys, and X. Fan, "Liquid core optical ring resonator label-free biosensor array for lab-on-a-chip development," Smart Medical and Biomedical Sensor Technology IV, Brian M. Cullum and J. Chance Carter, ed., Proc. SPIE 6380, 63800F, 2006.

[56] I. M. White, H. Zhu, H. Oveys, and X. Fan, "Bio/chemical sensors based on liquid core optical ring resonator," Micro (MEMS) and Nanotechnologies for Space Applications, Thomas George and Zhong-Yang Cheng, ed., Proc. SPIE 6223, 62230F, 2006.

[57] J. D. Suter, I. M. White, H. Zhu, and X. Fan, "Thermal Characterization of Liquid Core Optical Ring Resonator Sensors," Appl. Opt., in press.

[58] H. Zhu, I. M. White, J. D. Suter, M. Zourob, and X. Fan, "An Integrated Refractive Index Optical Ring Resonator Detector for Capillary Electrophoresis," Anal. Chem., in press.

[59] I. M. White, H. Zhu, J. D. Suter, N. M. Hanumegowda, H. Oveys, M. Zourob, and X. Fan, "Refractometric Sensors for Lab-on-a-Chip Based on Optical Ring Resonators," IEEE Sens. J., in press.

[60] I. M. White, H. Oveys, X. Fan, T. L. Smith, and J. Zhang, "Demonstration of a liquid core optical ring resonator sensor coupled with an ARROW waveguide array," Integrated Optics: Devices, Materials, and Technologies XI, Yakov Sidorin and Christoph A. Waechter, ed., Proc. SPIE 6475, 6475-6403, 2006.

[61] M. Y. Balakirev, S. Porte, M. Vemaz-Gris, M. Berger, J.-P. Arie, B. Fouque, and F. Chatelain, "Photochemical Patterning of Biological Molecules Inside a Glass Capillary," Anal. Chem, 77, 5474-5479, 2005.

[62] F. S. Ligler, M. Breimer, J. P. Golden, D. A. Nivens, J. P. Dodson, T. M. Green, D. P. Haders, and O. A. Sadik, "Integrating Waveguide Biosensor," Anal. Chem., 74, 713-719, 2002.

[63] M. A. Holden, S.-Y. Jung, and P. S. Cremer, "Patterning Enzymes Inside Microfluidic Channels via Photoattachment Chemistry," Anal. Chem., 76, 1838-1843, 2004.

[64] M. K. Chin and S. T. Ho, "Design and Modeling of Waveguide-Coupled Single-Mode Microring Resonators," J. Lightwave Technol., 16, 1433-1446, 1998.

[65] D. R. Linde, The CRC Handbook of Chemistry and Physics, CRC Press, 2005.

[66] J. P. Longtin and C.-H. Fan, "Precision laser-based concentration and refractive index measurement of liquid," Microscale Thermophys. Eng., 2, 261-272, 1998.

[67] M. Sumetsky and Y. Dulashko, "Sensing an optical fiber surface by a microfiber with angstrom accuracy," OFC, ed., OTuL6-1-OTuL6-3, 2006.

[68] A. E. Siegman, Lasers, University Science Books, Sausalito, Calif., 1986.

[69] A. D. Fitt, K. Furusawa, T. M. Monro, and C. P. Please, "Modeling the Fabrication of Hollow Fibers: Capillary Drawing," J. Lightwave Technol., 19, 1924-1931, 2001.

[70] S. C. Xue, R. I. Tanner, G. W. Barton, R. Lwin, M. C. J. Large, and L. Poladian, "Fabrication of microstructured optical fibers-part I: problem formulation and numerical modeling of transient draw process," J. Lightwave Technol., 23, 2245-2254, 2005.

[71] S. C. Xue, R. I. Tanner, G. W. Barton, R. Lwin, M. C. J. Large, and L. Poladian, "Fabrication of Microstructured Optical Fibers—Part II: Numerical Modeling of Steady-State Draw Process," J. Lightwave Technol., 23, 2255-2266, 2005.

[72] S. C. Xue, M. C. J. Large, G. W. Barton, R. I. Tanner, L. Poladian, and R. Lwin, "Role of Material Properties and Drawing Conditions in the Fabrication of Microstructured Optical Fibers," J. Lightwave Technol., 24, 853-860, 2006.

[73] Y. Matsuura, R. Kasahara, T. Katagiri, and M. Miyagi, "Hollow infrared fibers fabricated by glass-drawing technique," Optics Express, 10, 488-492, 2002.

[74] G. J. Wegner, A. W. Wark, H. J. Lee, E. Codner, T. Saeki, S. Fang, and R. M. Corn, "Real-Time Surface Plasmon Resonance Imaging Measurements for the Multiplexed Determination of Protein Adsorption/Desorption Kinetics and Surface Enzymatic Reactions on Peptide Microarrays," Anal. Chem., 76, 5677-5684, 2004.

[75] A. A. Ghoreyshi, F. A. Farhadpour, M. Soltanieh, and A. Bansal, "Transport of small polar molecules across nonporous polymeric membranes," Journal of Membr. Sci., 211, 193-214, 2003.

[76] J. Scheuer and A. Yariv, "Optical annular resonators based on radial Bragg and photonic crystal reflectors," Opt. Express, 11, 2003.

[77] S. D. Hart, G. R. Maskaly, B. Temelkuran, P. H. Prideaux, J. D. Joannopoulos, and Y. Fink, "External Refection from Omnidirectional Dielectric Mirror Fibers," Science, 296, 510-513, 2002.

[78] N. M. Litchinitser, A. K. Abeeluck, C. Headley, and B. J. Eggleton, "Antiresonant reflecting photonic crystal optical waveguides," Opt. Lett., 27, 1592-1594, 2002.

[79] R. E. Harrington, "Flow birefringence of persistence length deoxyribonucleic acid. Hydrodynamic properties, optical anisotropy, and hydration shell anisotropy," J. Am. Chem. Soc., 92, 6957-6964, 1970.

[80] T. Arakawa and Y. Kita, "Refractive Index of Proteins in Organic Solvents," Anal. Biochem., 271, 119-120, 1999.

[81] M. A. Duguay, Y. Kokubun, T. L. Koch, and L. Pfeiffer, "Antiresonant reflecting optical waveguides in SiO2— Si multilayer structures," Appl. Phys. Lett., 49, 13-15, 1986.

[82] T. Baba, Y. Kokubun, T. Sakaki, and K. Iga, "Loss Reduction of an ARROW Waveguide in Shorter Wavelength and Its Stack Configuration," J. Lightwave Technol., 6, 1440-1445, 1988.

[83] B. E. Little, J.-P. Laine, D. R. Lim, H. A. Haus, L. C. Kimerling, and S. T. Chu, "Pedestal antiresonant reflecting waveguides for robust coupling to microsphere resonators and for microphotonic circuits," Opt. Lett., 25, 73-75, 2000.

[84] J.-P. Laine, B. E. Little, D. R. Lim, H. C. Tapalian, L. C. Kimerling, and H. A. Haus, "Microsphere Resonator Mode Characterization by Pedestal Anti-Resonant Reflecting Waveguide," IEEE Photon. Technol. Lett., 12, 1004-1006, 2000.

[85] J. P. Laine, B. E. Little, D. R. Lim, H. C. Tapalian, L. C. Kimerling, and H. A. Haus, "Planar integrated wavelength-drop device based on pedestal antiresonant reflecting waveguides and high-Q silica microspheres," Opt. Lett., 25, 1636-1638, 2000.

[86] D. Erickson, X. Heng, Z. Li, T. Rockwood, T. Emery, Z. Zhang, A. Scherer, C. Yang, and D. Psaltis, "Optofluidics," Optical Information Systems III, Bahram Javidi and Demetri Psaltis, ed., Proc. SPIE 5908, 59080S, 2005.

[87] D. Psaltis, S. R. Quake, and C. Yang, "Developing optofluidic technology through the fusion of microfluidics and optics," Nature Materials, 442, 381-386, 2006.

[88] Q. Kou, I. Yesilyurt, and Y. Chen, "Collinear dual-color laser emission from a microfluidic dye laser," Appl. Phys. Lett., 88, 091101, 2006.

[89] Z. Li, Z. Zhang, A. Scherer, and D. Psaltis, "Mechanically tunable optofluidic distributed feedback dye laser," Opt. Express, 14, 10494-10499, 2006.

[90] Fan et al. "Overview of novel integrated optical ring resonator bio/chemical sensors," Proc. SPIE 6452, 64520M 1-20 (2007).

What is claimed is:

1. A hollow core optical ring resonator sensor comprising:
   (a) an optical tube with an outer surface and an inner surface, whereby the inner surface forms a hollow core, wherein the outer and inner surfaces of the optical tube are smooth;
   (b) an outer diameter of the optical tube ranging from about 10 µm to about 1000 µm; and,
   (c) a wall thickness of the optical tube ranging from about 1 µm to about 20 µm, wherein the optical tube is dimensioned so there will be a differential pressure below 10 Pa when a sample is present in the hollow core.

2. The hollow core optical ring resonator sensor of claim 1, wherein the optical tube has an outer diameter ranging from about 30 µm to about 500 µm.

3. The hollow core optical ring resonator sensor of claim 1, wherein the optical tube has an outer diameter ranging from about 50 µm to about 300 µm.

4. The hollow core optical ring resonator sensor of claim 1, wherein the optical tube has a wall thickness ranging from about 1 µm to about 10 µm.

5. The hollow core optical ring resonator sensor of claim 1, wherein the optical tube has a wall thickness ranging from about 2 µm to about 5 µm.

6. The hollow core optical ring resonator sensor of claim 1, further comprising a sample comprising a liquid or gas in contact with the inner surface of the optical tube.

7. The hollow core optical ring resonator sensor of claim 1, wherein the optical tube is contacted with a light source.

8. The hollow core optical ring resonator sensor of claim 1, the optical tube formed from a composition selected from the group consisting of: dielectric materials, glass, quartz, fused silica, borosilicate, optical plastics, polymer materials, PDMS, semiconductor materials, GaAs, InGaAs, photonic crystal structures, or any mixtures thereof.

9. The hollow core optical ring resonator sensor of claim 1, wherein the optical tube is contacted with a fiber taper.

10. The hollow core optical ring resonator sensor of claim 9, wherein the optical tube is transverse to the fiber taper.

11. The hollow core optical ring resonator sensor of claim 1, further comprising:
    (a) a photodetector; and
    (b) a data acquisition (DAQ) card in a computer.

12. The hollow core optical ring resonator sensor of claim 1, further comprising: an analyte substrate that is capable of binding a target analyte, wherein the analyte substrate is located within a fluidic channel formed by the inner surface of the optical tube.

13. The hollow core optical ring resonator sensor of claim 12, wherein the analyte substrate is affixed to the inner surface of the optical tube.

14. The hollow core optical ring resonator sensor of claim 1, wherein the optical tube is part of a multiplex device.

15. The hollow core optical ring resonator sensor of claim 1, wherein the optical tube is part of a chromatography device.

16. The hollow core optical ring resonator sensor of claim 1, further comprising a voltage source associated with a capillary electrophoresis device.

17. A hollow core optical ring resonator sensing architecture comprising:
    (a) an optical tube with a hollow core, with the optical tube having an outer diameter ranging from about 10 µm to about 1000 µm and a wall thickness ranging from about 1 µm to about 20 µm, wherein the optical tube is dimensioned so there will be a differential pressure below 10 Pa when a sample is present in the hollow core;
    (b) a guided light source in contact with the optical tube of (a), wherein the light source produces an optical signal in the optical tube, the optical signal comprising whispering gallery modes and an associated evanescent field; and
    (c) an optical signal that in communication with the interior of the hollow core, wherein the presence of a target analyte in the hollow core will cause modulations in the optical signal; and
    (d) a photodetector that is in contact with the resulting optical signal.

18. The hollow core optical ring resonator sensing architecture of claim 17, wherein an optical tube with a hollow core is associated with another optical tube with a hollow core as part of a multiplex device, and at some point the optical tubes are separated by at least about 100 µm.

19. A method of fabricating a hollow core optical ring sensor comprising:
(a) mechanically pulling an optical tube under high temperature, thereby producing an optical tube with an outer diameter ranging from about 10 µm to about 1000 µm; and,
(b) etching a surface of the optical tube with a solution comprising acids, thereby producing a wall thickness ranging from about 1 µm to about 20 µm, wherein the optical tube is dimensioned so there will be a differential pressure below 10 Pa when a sample is present in the hollow core.

20. A method of fabricating a hollow core optical ring comprising:
(a) mechanically pulling an optical tube under high temperature, thereby producing an optical tube with an outer diameter ranging from about 10 µm to about 1000 µm; and
(b) ablating a surface of the optical tube with a laser, thereby producing a wall thickness ranging from about 1 µm to about 20 µm, wherein the optical tube is dimensioned so there will be a differential pressure below 10 Pa when a sample is present in the hollow core.

21. A method of detecting a target analyte comprising the following steps:
(a) contacting a test sample to the inner surface of an optical tube with a hollow core, with the optical tube having an outer diameter ranging from about 10 µm to about 1000 µm and a wall thickness ranging from about 1 µm to about 20 µm, wherein the optical tube is dimensioned so there will be a differential pressure below 10 Pa when a sample is present in the hollow core;
(b) contacting a light of a known wavelength to the optical tube with a hollow core, thereby producing an associated evanescent field which is capable of extending into the hollow core, and an associated whispering gallery mode that is measurable as an optical signal output;
(c) measuring the optical signal output; and,
(d) detecting the presence of a target analyte in the test sample by comparing the optical signal output and the guided light input.

22. A hollow core optical ring resonator sensor system comprising:
(a) an optical tube with a hollow core, with the optical tube having an outer diameter ranging from about 10 µm to about 1000 µm and a wall thickness ranging from about 1 µm to about 20 µm, wherein the optical tube is dimensioned so there will be a differential pressure below 10 Pa when a sample is present in the hollow core;
(b) a light source capable of emitting light at a single wavelength or plurality of wavelengths, wherein the light source is positioned to emit light into the optical tube, the optical tube emitting at least a portion of the light therefrom, and
(c) a detector detecting the light emitted from the optical tube.

23. A hollow core optical ring resonator sensor comprising:
(a) an optical tube with an outer surface and an inner surface, whereby the inner surface forms a hollow core, wherein the outer and inner surfaces of the optical tube are smooth;
(b) an outer diameter of the optical tube ranging from about 10 µm to about 1000 µm; and,
(c) a wall thickness of the optical tube ranging from about 1 µm to about 20 µm, wherein the optical tube is dimensioned so that a light signal in the optical ring resonator will penetrate and interact with the hollow core, and wherein the optical tube is dimensioned so there will be a differential pressure below 10 Pa when a sample is present in the hollow core.

24. The hollow core optical ring resonator sensor of claim 23, wherein the optical tube has been mechanically pulled and has a bulge-shape or varying diameter.

* * * * *